(12) United States Patent
Rollat et al.

(10) Patent No.: US 7,122,175 B2
(45) Date of Patent: *Oct. 17, 2006

(54) RESHAPABLE HAIR STYLING COMPOSITION COMPRISING (METH)ACRYLIC COPOLYMERS OF FOUR OR MORE MONOMERS

(75) Inventors: Isabelle Rollat, Paris (FR); Henri Samain, Bièvres (FR); Olivier Morel, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/395,064

(22) Filed: Mar. 25, 2003

(65) Prior Publication Data

US 2003/0147836 A1    Aug. 7, 2003

Related U.S. Application Data

(63) Continuation of application No. 09/886,009, filed on Jun. 22, 2001, now Pat. No. 6,645,478.

(51) Int. Cl.
    A61Q 5/06    (2006.01)
(52) U.S. Cl. ...................... 424/70.2; 424/70.11; 424/47
(58) Field of Classification Search ................ 424/702; 526/266
    See application file for complete search history.

(56) References Cited

U.S. PATENT DOCUMENTS

| | | | |
|---|---|---|---|
| 3,577,517 A | 5/1971 | Kubot et al. |
| 3,660,561 A | 5/1972 | Shepherd et al. |
| 3,697,643 A | 10/1972 | Shepherd et al. |
| RE29,871 E | 12/1978 | Papantoniou et al. |
| 4,172,122 A | 10/1979 | Kubik et al. |
| 4,196,190 A | 4/1980 | Gehman et al. |
| 4,300,580 A | 11/1981 | O'Neill et al. |
| 4,358,567 A | 11/1982 | Hayama et al. |
| 4,552,755 A | 11/1985 | Randen |
| 4,762,703 A | 8/1988 | Abrutyn |
| 4,859,455 A | 8/1989 | Nowak, Jr. et al. |
| 4,963,348 A | 10/1990 | Bolich et al. |
| 4,978,527 A | 12/1990 | Brink et al. |
| 4,985,239 A | 1/1991 | Yahagi et al. |
| 5,019,377 A | 5/1991 | Torgerson |
| 5,026,540 A | 6/1991 | Dixon et al. |
| 5,039,519 A | 8/1991 | Inoue et al. |
| 5,104,642 A | 4/1992 | Wells et al. |
| 5,120,531 A | 6/1992 | Wells et al. |
| 5,120,532 A | 6/1992 | Wells et al. |
| 5,171,807 A | 12/1992 | Kopolow |
| 5,173,291 A | 12/1992 | Brink et al. |
| 5,219,559 A | 6/1993 | Kopolow |
| 5,238,736 A | 8/1993 | Tseng et al. |
| 5,278,269 A | 1/1994 | Mita et al. |
| 5,413,775 A | 5/1995 | Hatfield et al. |
| 5,441,728 A | 8/1995 | Tsauer et al. |
| 5,441,730 A | 8/1995 | Gough et al. |
| 5,460,804 A | 10/1995 | Krzysik |
| 5,501,851 A | 3/1996 | Mudge et al. |
| 5,516,508 A | 5/1996 | Thaman et al. |
| 5,518,712 A | 5/1996 | Stewart |
| 5,547,659 A | 8/1996 | Rinaldi et al. |
| 5,589,157 A | 12/1996 | Hatfield |
| 5,620,683 A | 4/1997 | Tong et al. |
| 5,658,558 A | 8/1997 | Schwartz |
| 5,662,892 A | 9/1997 | Bolich, Jr. et al. |
| 5,688,493 A | 11/1997 | Sugawara et al. |
| 5,730,966 A | 3/1998 | Torgerson et al. |
| 5,938,058 A | 8/1999 | Kim |
| 5,961,989 A | 10/1999 | Mougin et al. |
| 5,968,495 A | 10/1999 | Bolich, Jr. et al. |
| 5,989,570 A | 11/1999 | Lion et al. |
| 5,997,886 A | 12/1999 | Peffly et al. |
| 6,013,722 A | 1/2000 | Yang et al. |
| 6,060,072 A | 5/2000 | Konik et al. |
| 6,126,929 A | 10/2000 | Mougin et al. |
| 6,149,898 A | 11/2000 | Peffly et al. |
| 6,168,866 B1 | 1/2001 | Clark |
| 6,214,328 B1 * | 4/2001 | Chang et al. ............ 424/70.16 |
| 6,294,158 B1 | 9/2001 | Dupuis |
| 6,346,234 B1 | 2/2002 | Rollat et al. |
| 6,368,575 B1 | 4/2002 | Chang et al. |
| 6,645,478 B1 * | 11/2003 | Rollat et al. ............... 424/70.1 |
| 6,667,378 B1 * | 12/2003 | Rollat et al. ............... 526/266 |
| 6,689,346 B1 * | 2/2004 | Rollat et al. ............... 424/70.1 |
| 2002/0004035 A1 | 1/2002 | Bhatt et al. |
| 2002/0058754 A1 | 5/2002 | Engel et al. |

(Continued)

FOREIGN PATENT DOCUMENTS

EP    0 201 342    12/1986

(Continued)

OTHER PUBLICATIONS

Derwent Abstract of EP 0 761 199.

(Continued)

*Primary Examiner*—Jyothsna Venkat
(74) *Attorney, Agent, or Firm*—Finnegan, Henderson, Farabow, Garrett & Dunner, L.L.P.

(57) ABSTRACT

A reshapable hair styling composition comprising at least one (meth)acrylic copolymer comprising: (a) units derived from at least one monomer chosen from (meth)acrylate esters of branched and straight chain alkyl alcohols, (b) units derived from at least one monomer chosen from (meth) acrylate esters of saturated and unsaturated cyclic alcohols containing 6 to 20 carbon atoms, (c) optionally units derived from at least one monomer chosen from hydrophilic monomers, and (d) optionally units derived from at least one monomer other than (a), (b), and (c) monomers, wherein said at least one (meth)acrylic copolymer comprises units derived from at least four different monomers and wherein said composition provides a reshapable effect.

57 Claims, No Drawings

U.S. PATENT DOCUMENTS

| | | |
|---|---|---|
| 2002/0076390 A1 | 6/2002 | Kantner et al. |
| 2003/0147833 A1 | 8/2003 | Rollat et al. |

FOREIGN PATENT DOCUMENTS

| | | |
|---|---|---|
| EP | 0 299 025 | 1/1989 |
| EP | 0 524 346 | 1/1993 |
| EP | 0 694 565 | 1/1996 |
| EP | 0 985 401 | 3/2000 |
| EP | 0 985 405 | 3/2000 |
| EP | 1 201 223 | 5/2002 |
| JP | 48-48648 | 7/1973 |
| JP | 56-90006 | 7/1981 |
| JP | 57-50912 | 3/1982 |
| JP | 10-95714 | 4/1998 |
| JP | 10-203937 | 8/1998 |
| JP | 2004-512292 A | 4/2004 |
| WO | WO 93/06816 | 4/1993 |
| WO | WO 94/02112 | 2/1994 |
| WO | WO 97/33555 | 9/1997 |
| WO | WO 97/33557 | 9/1997 |
| WO | WO 98/24825 | 6/1998 |
| WO | WO 98/25710 | 6/1998 |
| WO | WO 98/38969 | 9/1998 |
| WO | WO 98/51266 | 11/1998 |
| WO | WO 99/08652 | 2/1999 |
| WO | WO 99/63954 | 12/1999 |
| WO | WO 00/57846 | 10/2000 |
| WO | WO 02/09656 | 2/2002 |
| WO | WO 02/34218 | 5/2002 |

OTHER PUBLICATIONS

Derwent Abstract of EP 1 174 113.
EPO Apr. 3, 2003 Search Report for EP 02 29 3142.
EP Search Report for EP 02 29 3039, dated Feb. 27, 2003.
PCT Search Report for WO 02/03275, dated Jan. 20, 2003.
Jachowicz et al., "Dynamic Hairspray Analysis," 52(5) Journal of Cosmetic Science, 281-295 (Sep. 2001).
Office Action in co-pending U.S. Appl. No. 09/627,055, dated May 27, 2005 (Ex. Venkat).
Office Action in co-pending U.S. Appl. No. 10/022,253, dated May 24, 2005 (Ex. Venkat).
Derwent Abstract of JP 10-95714.
Derwent Abstract of JP 10-203937.
Derwent Abstract of JP 48-48648.
Derwent Abstract of JP 56-90006.
Derwent Abstract of JP 57-50912.
English language translation of JP 10-203937.
Dialog Abstract of JP 10-203937.
Co-pending U.S. Appl. No. 09/627,121, filed Jul. 27, 2000, Inventors: Isabelle Rollat et al., Title: Reshapable Hair Styling Composition Comprising Aqueous Colloidal Dispersions of Sulfonated Polyurethane Urea.
Co-pending U.S. Appl. No. 09/627,055, filed Jul. 27, 2000, Inventors: Isabelle Rollat et al., Title: Reshapable Hair Styling Composition Comprising Acrylic Emulsions.
Co-pending U.S. Appl. No. 09/627,785, filed Jul. 27, 2000, Inventors: Isabelle Rollat et al., Title: Reshapable Hair Styling Composition Comprising Polyurethane Dispersions.
Co-pending U.S. Appl. No. 09/695,392, filed Oct. 25, 2000, Inventors: Isabelle Rollat et al., Title: Reshapable Hair Styling Compositions Comprising Acrylic Emulsions.
Co-pending U.S. Appl. No. 09/769,311, filed Jan. 26, 2001, Inventors: Isabelle Rollat et al., Title: Reshapable Hair Styling Composition Comprising Silicon-Containing Polycondensates.
Co-pending U.S. Appl. No. 09/866,013, filed Jun. 22, 2001, Inventors: Isabelle Rollat et al., Title: Reshapable Hair Styling Composition Comprising Heterogeneous (Meth)Acrylic Copolymer Particles,
Co-pending U.S. Appl. No. 10/023,330, filed Dec. 20, 2001, Inventors: Isabelle Rollat et al., Title: Reshapable Hair Styling Rinse Composition Comprising (Meth)Acrylic Copolymers.
Co-pending U.S. Appl. No. 10/022,253, filed Dec. 20, 2001, Inventors: Isabelle Rollat et al., Title: Reshapable Hair Styling Non-Rinse Composition Comprising (Methy)Acrylic Copolymers.

* cited by examiner

RESHAPABLE HAIR STYLING COMPOSITION COMPRISING (METH)ACRYLIC COPOLYMERS OF FOUR OR MORE MONOMERS

This application is a continuation of application Ser. No. 09/886,009, filed Jun. 22, 2001, now U.S. Pat. No. 6,645,478, which is incorporated herein by reference.

The present invention relates to a reshapable hair styling composition.

Fixing the hairstyle is an important element in hair styling, and involves maintaining a shaping that has already been carried out, or simultaneously shaping and fixing the hair.

In accordance with the invention, the term "hair styling composition" relates to any kind of hair composition that can be used to effect hair styling, for example fixing compositions, shampoos, conditioners, permanent waving compositions, hair care products, and hair treatment products.

The most prevalent hair styling compositions on the cosmetic market for shaping and/or maintaining the hairstyle are spray compositions comprising a solution, usually alcohol- or water-based, and one or more materials, generally polymer resins. One of the functions of polymer resins is to form links between the hairs, these materials also being called fixatives, in a mixture with various cosmetic adjuvants. This solution is generally packaged either in an appropriate aerosol container, which is pressurized with the aid of a propellant, or in a pump flask.

Some other known hair styling compositions include styling gels and mousses, which are generally applied to the wetted hair before brushing or setting it. In contrast to the conventional aerosol lacquers, some types of these other known hair styling compositions disadvantageously are not designed to allow the hair to be fixed in a shape created before their application. In fact, these compositions are essentially aqueous and their application wets the hair; hence these compositions are not designed to maintain the initial shape of the hairstyle. In order to shape and fix the hairstyle, therefore, it is necessary to carry out subsequent brushing and/or drying with these types of compositions.

Thus, many hair styling compositions exist that have the same disadvantage: they are not designed to allow the hairstyle to be later modified to a desired shape, which is other than that formed initially, without starting the styling and fixing operations again. Moreover, under various kinds of stress, the hairstyle has a tendency to take on an undesirable permanent set, which cannot easily be modified. Also in the styling process, one desires hair conditioning benefits, such as ease of combing and soft hair feel appearance.

A subject of the invention is a reshapable hair styling composition comprising at least one (meth)acrylic copolymer comprising: (a) optional units derived from at least one monomer chosen from (meth)acrylate esters of branched and straight chain alkyl alcohols, (b) optional units derived from at least one monomer chosen from (meth)acrylate esters of saturated and unsaturated cyclic alcohols containing 6 to 20 carbon atoms, (c) optional units derived from at least one monomer chosen from hydrophilic monomers, or (d) optional units derived from at least one monomer other than said (a), (b), and (c) monomers, wherein said at least one (meth)acrylic copolymer comprises units derived from at least four different monomers, wherein said at least one (meth)acrylic copolymer comprises at least one unit derived from monomers recited in either (a) or (b), and wherein said composition provides a reshapable effect.

Another subject of the invention is a reshapable hair styling composition comprising at least one (meth)acrylic copolymer comprising: (a) units derived from at least one monomer chosen from (meth)acrylate esters of branched and straight chain alkyl alcohols, (b) units derived from at least one monomer chosen from (meth)acrylate esters of saturated and unsaturated cyclic alcohols containing 6 to 20 carbon atoms, (c) optional units derived from at least one monomer chosen from hydrophilic monomers, and (d) optional units derived from at least one monomer other than said (a), (b), and (c) monomers, wherein said at least one (meth)acrylic copolymer comprises units derived from at least four different monomers and wherein said composition provides a reshapable effect.

Another subject of the invention is a reshapable hair styling composition comprising at least one (meth)acrylic copolymer comprising: (a) from about 10 to about 85 weight percent of units derived from at least one monomer chosen from (meth)acrylate esters of branched and straight chain alkyl alcohols, (b) from about 5 to about 70 weight percent of units derived from at least one monomer chosen from (meth)acrylate esters of saturated and unsaturated cyclic alcohols containing 6 to 20 carbon atoms, (c) from 0 to about 20 weight percent of units derived from at least one monomer chosen from hydrophilic monomers, and (d) from 0 to about 20 weight percent of units derived from at least one monomer other than said (a), (b), and (c) monomers, wherein said at least one (meth)acrylic copolymer comprises units derived from at least four different monomers and wherein said composition provides a reshapable effect.

Another subject of the invention is a reshapable hair styling composition comprising at least one (meth)acrylic copolymer comprising: (a) from about 20 to about 80 weight percent of units derived from ethyl hexyl (meth)acrylate, (b) from about 5 to about 65 weight percent of units derived from isobornyl (meth)acrylate, (c) from about 1 to about 15 weight percent of units derived from acrylic acid, and (d) from about 1 to about 15 weight percent of units derived from methacrylic acid, wherein the ratio of ethyl hexyl (meth)acrylate derived units to isobornyl acrylate derived units ranges from about 0.5:1 to about 6:1, wherein said composition provides a reshapable effect.

The weight percentages of the (a), (b), (c), and (d) units may be based on the total weight of each monomer type used compared to the total weight of all monomers used.

Another subject of the invention is a reshapable hair styling composition comprising at least one (meth)acrylic copolymer, as described above, wherein said reshapable hair styling composition is in the form of a spray, aerosol, mousse, gel, stick, mud, or lotion.

Another subject of the invention is an aerosol device comprising a vessel, which comprises: (1) an aerosol composition, which provides a reshapable effect and comprises a liquid phase comprising at least one composition comprising at least one (meth)acrylic copolymer, as described above, and a propellant, and (2) a dispenser.

Another subject of the invention is a method of cosmetically treating hair, comprising applying to the hair before, during, or after shaping of a hairstyle of said hair a composition comprising at least one (meth)acrylic copolymer, as described above, wherein said composition provides a reshapable effect.

Another subject of the invention is a method of reshaping hair, comprising: (1) applying to the hair before, during, or after the initial shaping of the hairstyle a composition comprising at least one (meth)acrylic copolymer, as described above, wherein said composition provides a reshapable effect, and (2) thereafter shaping the hairstyle at least once, wherein no additional composition or heat is added.

Another subject of the invention is a method of manufacturing a reshapable hair styling composition comprising including in a hair styling composition at least one (meth) acrylic copolymer, as described above, wherein said at least one (meth)acrylic copolymer is present in an amount effective to provide a reshapable effect.

In one embodiment of the invention, such reshapable hair styling compositions may be in the form of an aqueous emulsion or dispersion. All emulsions comprise a continuous phase and at least one dispersed phase. The term "dispersion" means generally a multi-phase system where at least one phase contains discrete particles distributed throughout a bulk substance. A portion of the copolymer may exist as the discrete particle in an aqueous phase. Dispersions are possible through the use of certain components that are insoluble in the aqueous system. By "dispersion," it is also meant that not necessarily the entire copolymer needs to be water insoluble; some of the copolymer can be soluble in the aqueous mixture. It may be desirable that a dispersion remains stable under ambient conditions. In one embodiment, dispersions are stable at room temperature for more than 30 days, such as for more than 90 days, for more than 180 days, and for more than 360 days. A dispersion is deemed stable so long as the discrete particles of the internal phase remain distributed throughout the bulk substance (external phase).

In one embodiment, such dispersions may be blended with other dispersions or with other known additives such as fillers, plasticizers, pigments (such as carbon black), silica sols and other known leveling agents, wetting agents, antifoaming agents, and stabilizers.

The term "(meth)acrylate" is used to encompass both of the terms acrylate and methacrylate. Similarly, the term "(meth)acrylic acid" is used to encompass both of the terms acrylic acid and methacrylic acid.

The term "reshapable" hair styling composition means a hair styling composition providing hair styling that can be restored or modified without new material or heat being applied. For example, in order to restore or modify the hairstyle in case of "drooping" or loss of setting (dishevelment), no new materials, such as water or any form of fixing agent, or heat are required. Thus, to provide a "reshapable" effect means to provide a hair styling that can be restored or modified without new material or heat being applied. The efficacy of the composition can be long lasting, such as 10–24 hours, giving rise to a durable styling effect. Other terms, which may be synonymous with reshapable, include repositionable, remoldable, restyleable, rearrangable, and remodelable.

In general, the monomers recited in (a) constitute, for example, from about 10 to about 85 weight percent of the total amount of monomers used. In one embodiment, they may constitute from about 20 to about 80 weight percent of the total amount of monomers used. The monomers recited in (a) may be chosen, for example, from (meth)acrylate esters of $C_1$ to $C_{30}$ branched and straight chain alkyl alcohols, such as from (meth)acrylate esters of $C_4$ to $C_{18}$ branched and straight chain alkyl alcohols. In one embodiment, the monomers recited in (a) may be chosen from isooctyl (meth)acrylate, n-butyl (meth)acrylate, isobutyl (meth)acrylate, t-butyl (meth)acrylate, 2-methylbutyl (meth)acrylate, 2-ethylhexyl (meth)acrylate, n-octyl (meth)acrylate, isononyl (meth)acrylate, lauryl (meth)acrylate, octadecyl (meth)acrylate, and mixtures thereof. In another embodiment, the monomers recited in (a) may be chosen from 2-ethylhexyl (meth)acrylate, n-butyl (meth)acrylate, isooctyl (meth)acrylate, 2-methylbutyl (meth)acrylate, and mixtures thereof.

The monomers recited in (b) generally have a higher $T_g$ than the monomers recited in (a). In general, they may constitute, for example, from about 5 to about 70 weight percent of the total amount of monomers used. In one embodiment, they may constitute from about 10 to about 70 weight percent of the total amount of monomers used. In another embodiment, they may constitute from about 5 to about 65 weight percent of the total amount of monomers used. The monomers recited in (b) may be chosen from (meth)acrylate esters of saturated and unsaturated cyclic alcohols containing 6 to 20 carbon atoms. In one embodiment, the monomers recited in (b) are chosen from monofunctional (meth)acrylate esters of bridged cycloalkyl alcohols, having 6 to 20 carbon atoms, and aromatic alcohols. The cycloalkyl and aromatic groups may be substituted by groups chosen from $C_1$ to $C_6$ alkyl, halogen, cyano groups, and the like. In another embodiment, the monomers recited in (b) are chosen from bicyclo[2.2.1]heptyl (meth)acrylate; adamantyl (meth)acrylate; 3,5-dimethyladamantyl (meth) acrylate; isobornyl (meth)acrylate; tolyl (meth)acrylate; phenyl (meth)acrylate; t-butylphenyl (meth)acrylate; 2-napthyl (meth)acrylate; benzyl (meth)acrylate; cyclohexyl (meth)acrylate; menthyl (meth)acrylate; 3,3,5-trimethylcyclohexyl (meth)acrylate; dicyclopentenyl (meth)acrylate; 2(dicyclopentenyloxy)ethyl (meth)acrylate; and mixtures thereof.

The optional monomers recited in (c) are hydrophilic monomers. In general, they may constitute, for example, from 0 to about 20 weight percent of the total amount of monomers used. In one embodiment, they may constitute from about 1 to about 15 weight percent of the total amount of monomers used. In another embodiment, they may constitute from about 1 to about 10 weight percent of the total amount of monomers used. In one embodiment, the monomers recited in (c) may be chosen from those monomers having hydroxyl, ether, amide, amine, carboxylic acid, sulfonic acid, and phosphonic acid functionalities. In another embodiment, the monomers recited in (c) may be chosen from (meth)acrylamide, 2-ethoxyethyl (meth)acrylate, mono (meth)acrylates of polyethylene glycol monoethers, N-vinyl-2-pyrrolidone, N-vinyl formamide, N-vinyl acetamide, 2-hydroxyethyl (meth)acrylate, hydroxypropyl (meth) acrylate, vinyl pyridine, N,N-diethylaminoethyl (meth)acrylate, N,N-dimethylaminoethyl (meth)acrylate, N-t-butylaminoethyl (meth)acrylate, acrylic acid, methacrylic acid, itaconic acid, maleic acid, fumaric acid, vinyl benzoic acid, 2-carboxyethyl (meth)acrylate, 2-sulfoethyl (meth) acrylate, and 4-vinyl phenyl phosphonic acid. In yet another embodiment, the monomers recited in (c) may be chosen from (meth)acrylic acid and N-vinyl-2-pyrrolidone.

The at least one (meth)acrylic copolymer may optionally include units derived from other monomers to improve performance, reduce cost, or for other purposes, provided that such monomers are used in an amount that does not compromise the composition's reshapable effect. In general, the optional monomers recited in (d) may constitute, for example, from 0 to about 20 weight percent of the total amount of monomers used. Examples of such other monomers may include vinyl esters, vinyl chlorides, vinylidene chlorides, styrenes, (meth)acrylate esters of $C_1$ to $C_3$ alkyl alcohols, macromolecular monomers such as monoacrylic functional polystyrene and polydimethylsiloxane, and the like.

The composition may further comprise a cosmetically acceptable vehicle. The choice of vehicle is adapted to the method of application selected. The cosmetic vehicle appropriate for hair may be chosen from water, water miscible solvents such as lower alcohols, e.g., $C_1$ to $C_4$ branched and straight chain aliphatic alcohols, and combinations thereof. In one embodiment, the vehicle is a lower alcohol chosen from ethanol, n-propanol, and 2-propanol (IPA). When water miscible solvents and water are present, the solvent to water ratio may range from about 20:80 to about 90:10 weight/weight, such as from about 30:70 to about 85:15.

The vehicle may also comprise additional solvents. For example, other rapid evaporating solvents may be used, such as hexamethyldisiloxane (HMDS); cyclic silicones ($D_4$ and $D_5$); $C_4$–$C_{10}$ alkanes including isoparafins such as Permethyl 97A and Isopar C; acetone; hydrofluoroethers (HFEs) and the like.

The composition may also comprise additives such as gelling agents, foaming agents, and silicones. It is understood that the person skilled in the art will know how to choose the additional constituents and their amount in the composition according to the invention, such as the constituents of the composition, so as not to adversely affect or substantially affect its reshapable hair styling properties.

The inventive copolymers of the present invention may be prepared using emulsion polymerization, solution polymerization followed by an inversion step, and suspension polymerization. These methods use initiators that, through various techniques, are decomposed to form free radicals. Once in their radical form, the initiators react with the monomers, starting the polymerization process. The initiators are often called "free radical initiators." Various decomposition methods for the initiators are discussed first, followed by a description of the emulsion, solution, and suspension polymerization methods.

The initiator can be decomposed homolytically to form free radicals. Homolytic decomposition of the initiator can be induced by using heat energy (thermolysis), using light energy (photolysis), and/or using appropriate catalysts. Light energy can be supplied by means of visible or ultraviolet sources, including low intensity fluorescent black light lamps, medium pressure mercury arc lamps, and germicidal mercury lamps.

Catalyst induced homolytic decomposition of the initiator typically involves an electron transfer mechanism, resulting in a reduction-oxidation (redox) reaction. This redox method of initiation is described in Elias, Chapter 20 (detailed below). Initiators such as persulfates, peroxides, and hydroperoxides are more susceptible to this type of decomposition. Useful catalysts include, but are not limited to (1) amines, (2) metal ions used in combination with peroxide or hydroperoxide initiators, and (3) bisulfite or mercapto-based compounds used in combination with persulfate initiators.

Presently, in certain embodiments of the invention, the method of initiation comprises thermolysis or catalysis. Thermolysis can provide ease of control of the reaction rate and exotherm.

Useful initiators are described in Chapters 20 & 21 Macromolecules, Vol. 2, 2nd Ed., H. G. Elias, Plenum Press, 1984, New York, the disclosure of which related to initiators is specifically incorporated herein by reference. Useful thermal initiators include, but are not limited to, the following: (1) azo compounds such as 2,2-azo-bis-(isobutyronitrile), dimethyl 2,2'-azo-bis-isobutyrate, azo-bis-(diphenyl methane), and 4-4'-azo-bis-(4-cyanopentanoic acid); (2) peroxides such as benzoyl peroxide, cumyl peroxide, tert-butyl peroxide, cyclohexanone peroxide, glutaric acid peroxide, lauroyl peroxide, and methyl ethyl ketone peroxide; (3) hydrogen peroxide and hydroperoxides such as tert-butyl hydroperoxide and cumene hydroperoxide; (4) peracids such as peracetic acid and perbenzoic acid; potassium persulfate; ammonium persulfate; and (5) peresters such as diisopropyl percarbonate.

Useful photochemical initiators include but are not limited to benzoin ethers such as diethoxyacetophenone, oximino-ketones, acylphosphine oxides, diaryl ketones such as benzophenone and 2-isopropyl thioxanthone, benzil and quinone derivatives, and 3-ketocoumarins as described by S. P. Pappas, J. Rad. Cur., July 1987, p. 6, the disclosure of which related to photochemical initiators is specifically incorporated herein by reference.

In one embodiment, the copolymers of the present invention can be made by emulsion polymerization, generally comprising a process where the monomers are dispersed in a continuous phase (typically water) with the aid of an emulsifier and polymerized with the free-radical initiators, described above. Other components that are often used in this process include stabilizers (e.g., copolymerizable surfactants), chain transfer agents for minimizing and/or controlling the copolymer molecular weight, and catalysts. The product of this type of polymerization is typically a colloidal dispersion of the copolymer particles, often referred to as a "latex." In one embodiment of an emulsion polymerization process, a redox chemistry catalyst, such as sodium metabisulfite, used in combination with potassium persulfate initiator and ferrous sulfate heptahydrate, is used to start the polymerization at or near room temperature. Typically, the copolymer particle size is less than one micrometer, such as less than 0.5 micrometer.

Emulsion polymerization can be carried out in several different processes. For example, in a batch process the components are charged into the reactor at or near the beginning. In a semi-continuous process, a portion of the monomer composition is initially polymerized to form a "seed" and the remaining monomer composition is metered in and reacted over an extended time. These emulsion polymerization techniques are well known by those skilled in the art and are widely used in industry.

In another embodiment, the copolymers of the present invention can be made by solution polymerization followed by an inversion step. In one illustrative solution polymerization method, the monomers and suitable inert solvents are charged into a reaction vessel. The monomers and the resultant copolymers are soluble in the solvent. After the monomers are charged, an initiator, such as a thermal free radical initiator, is added. The vessel is purged with nitrogen to create an inert atmosphere. The reaction is allowed to proceed, typically using elevated temperatures, to achieve a desired conversion of the monomers to the copolymer. In solution polymerization, the initiator used may comprise a thermally decomposed azo or peroxide compound for reasons of solubility and control of the reaction rate.

Suitable solvents for solution polymerizations include but are not limited to (1) esters such as ethyl acetate and butyl acetate; (2) ketones such as methyl ethyl ketone and acetone; (3) alcohols such as methanol and ethanol; (4) aliphatic and aromatic hydrocarbons; and (5) mixtures thereof. The solvent may be any substance which is liquid in a temperature range of about −10° C. to about 50° C., does not interfere with the energy source or catalyst used to dissociate the initiator to form free radicals, is inert to the reactants and product, and will not otherwise adversely affect the reaction. The amount of solvent, when used, is generally about 30 to about 80 percent by weight based on the total weight of the reactants and solvent. For example, the amount of solvent ranges from about 40 weight percent to about 65 weight percent, based upon the total weight of the reactants and solvent, to yield fast reaction times.

Copolymers prepared by solution polymerization can be inverted to yield dispersions of small average particle size, typically less than about one micrometer, such as less than about 0.5 micrometer. Inversion of copolymers can occur in an aqueous carrier or aqueous solvent provided that (1) they contain ionic functionality or (2) they contain acidic or basic functionality, which on neutralization yields ionic functionality.

Copolymers containing acidic functionality are obtained by copolymerizing acidic monomers. Suitable acidic monomers include those containing carboxylic acid functionality such as acrylic acid, methacrylic acid, itaconic acid, etc.; those containing sulfonic acid functionality such as 2-sulfoethyl methacrylate; and those containing phosphonic acid functionality. Preferred acidic monomers include acrylic acid and methacrylic acid.

Copolymers containing basic functionality are obtained by copolymerizing basic monomers. Suitable basic monomers include those containing amine functionality such as vinyl pyridine; N,N-diethylaminoethyl (meth)acrylate; N,N-dimethylaminoethyl (meth)acrylate; and N-t-butylaminoethyl (meth)acrylate. Examples of basic monomers are N,N-dimethylaminoethyl (meth)acrylates.

The copolymer may be prepared in a water-miscible solvent, which has a boiling point below 100° C., such as acetone or methyl ethyl ketone. Alternatively, a non-water-miscible polymerization solvent such as ethyl acetate may be used. The non-water-miscible polymerization solvent may be removed from the copolymer by using a rotary evaporator. The resulting copolymer can then be dissolved in a water-miscible solvent such as those described above or mixtures including isopropanol, methanol, ethanol, and tetrahydrofuran.

The resulting solutions are added with stirring to an aqueous solution of a base (in the case of copolymers containing the acidic functionality) or an acid (in the case of copolymers containing the basic functionality). Alternatively, the base or acid can be added to the polymer solution prior to adding water or being added to water. Suitable bases include (1) ammonia and organic amines, such as aminomethyl propanol, triethyl amine, triethanol amine, methyl amine, and morpholine, and (2) metal hydroxides, oxides, and carbonates, etc. Suitable acids include (1) carboxylic acids such as acetic acid, and (2) mineral acids, such as HCl. In the case of a volatile weak base (e.g., ammonia) or acid (e.g., acetic acid), the ionic group formed (an ammonium carboxylate) is non-permanent in nature. For example, for a (meth)acrylic acid containing copolymer neutralized with aqueous ammonia, the copolymer remains as the ammonium acrylate derivative when dispersed in water, but is thought to revert to its original free acid state as the coating dries on the surface. This is because there is equilibrium between the neutralized and free acid, which is shifted towards the free acid as the ammonia is driven off on drying.

In yet another embodiment, the copolymers of the present invention can be made by a suspension polymerization method. The suspension polymerization method for making the inventive copolymers can proceed in the absence of surfactants. Instead, colloidal silica in combination with a promoter may be used as the stabilizer. Using this process, surfactant-free copolymers can be obtained with a relatively narrow particle size distribution (such as, no greater than about 20%).

In one embodiment, the method for suspension polymerization involves making a monomer premix comprising the (a), (b), (c), and (d) monomers. The premix is combined with a water phase, such as deionized water, containing colloidal silica and a promoter. Amphiphilic polymers represent one class of useful promoters.

The pH of the mixture is adjusted so as to be in the range of 3 to 11, such as in the range of 4 to 6, without coagulation of the particles. For certain monomers, the initial pH of the mixture can be as low as about 2.5. This pH is low enough for the colloidal silica to stabilize the monomer droplet, but the final product may contain a small amount of coagulum. Similar observations can be made at high pH. It has been observed that when the mixture is treated with ammonia or hydrochloric acid to a pH ranging from about 4 to about 6, the reaction is more stable and the final product is basically free of coagulum.

The mixture is exposed to high shear, such as that capable in a Waring™ blender, to break the monomer droplets down to a diameter size of 1 micrometer or less. The shearing action is then reduced to a lower agitation (or temporarily stopped) to allow for the partial coalescence of the small droplets and formation of a suspension. Initiator is added. The silica-promoter mixture stabilizes the droplets and limits their coalescence yielding very uniform, and sometimes nearly monodisperse particles. The suspension polymerization is completed under moderate agitation and a stable, aqueous dispersion of (meth)acrylic particles is obtained.

The above described suspension polymerization has several advantages. For example, the method yields a copolymer with a narrow distribution of mean particle size and limited coalescence. When coalescence is present, the particles tend to migrate towards one another and can form large masses. Coalescence hampers the handling and transportation of the particles and thus is undesirable. The particles may be sterically stabilized by the colloidal silica.

Also, the method allows for copolymers that withstand freezing temperatures, allowing them to be redispersed after thawing. It has been discovered that the copolymer is stable, i.e., does not coalesce when the same volume of alcohol (methanol or isopropanol) and water is used in the dispersion.

In yet another embodiment of the invention, the (meth) acrylic copolymer has a glass transition temperature (Tg) ranging from about –100° C. to about 15° C. According to the present invention, the Tg of the (meth)acrylic copolymer is obtained following the application of the (meth)acrylic copolymer in a simplex vehicle to a substrate and then drying. The glass transition temperature is determined by the Differential Scanning Calorimetric method (DSC).

In one embodiment of the invention, the (meth)acrylic copolymer may be present in an amount ranging from about 0.1 to about 40, such as from about 0.5 to about 15, weight percent of the total weight of the composition in order to provide a reshapable effect.

The composition according to the invention may comprise one or more other constituents, which are conventional in cosmetics, chosen from preservatives; perfumes; active haircare agents; plasticizers; anionic, cationic, amphoteric (such as zwitterionic), and nonionic surfactants; hair conditioning agents such as silicone fluids, fatty esters, fatty alcohol, long chain hydrocarbons, emollients, lubricants, and penetrants such as lanolin compounds, protein hydrolysates, and other protein derivatives; anionic, cationic, amphoteric (such as zwitterionic), and nonionic polymers; dyes; tints; bleaches; reducing agents; pH adjusting agents; sunscreens (such as UV filters); and thickening agents.

In one embodiment, the one or more constituents are chosen from polymeric adhesives, for example fixing polymers, such as anionic, cationic, amphoteric (such as zwitterionic) and nonionic fixing polymers and combinations thereof. As used herein, the term "polymer" refers to homopolymers and copolymers, which are derived from more than one type of monomer, such as from two, three, four, or more different monomer types.

The cationic fixing polymers comprise cationic moieties or moieties that are convertible to cationic moieties. Suitable examples of cationic fixing polymers, which can be used according to the present invention, are those that may be chosen from polymers comprising at least one group chosen from primary amine groups, secondary amine groups, tertiary amine groups, and quaternary amine groups, wherein the at least one group forms part of the polymer chain or is linked directly to it, having a weight average molecular weight ranging from about 500 to about 5,000,000, such as from about 100 to about 3,000,000.

Among these polymers, mention may be made more particularly of the following cationic fixing polymers:

(1) homopolymers and copolymers derived from monomers chosen from (meth)acrylic esters and (meth)acrylic amides comprising units of at least one of the following formulae:

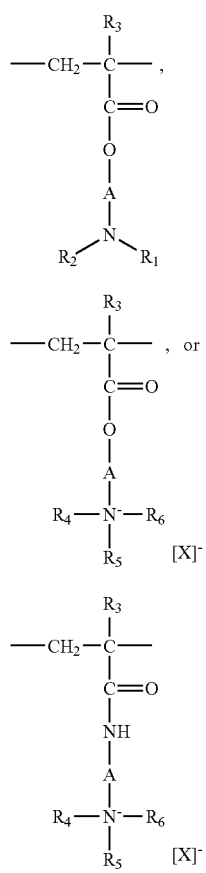

in which each $R_3$ is independently chosen from hydrogen and $CH_3$ groups; each A is independently chosen from linear and branched alkyl groups comprising 1 to 6 carbon atoms and hydroxyalkyl groups comprising 1 to 4 carbon atoms; each $R_4$, $R_5$, and $R_6$ is independently chosen from alkyl groups comprising 1 to 18 carbon atoms and benzyl radicals; each $R_1$ and $R_2$ is independently chosen from hydrogen and alkyl groups comprising 1 to 6 carbon atoms; and each $X^-$ is independently chosen from methyl sulphate anions and halide anions, such as chloride or bromide anions.

In one embodiment, the copolymers of family (1) further comprise at least one unit derived from monomers chosen from (meth)acrylamides, diacetone (meth)acrylamides, (meth)acrylamides substituted on the nitrogen by a group chosen from lower alkyls, (meth)acrylic acids, esters of (meth)acrylic acids, vinyllactams such as vinylpyrrolidone and vinyl-caprolactam, and vinyl esters.

Thus, mention may be made, among these cationic copolymers of the family (1), of:

copolymers of acrylamide and of dimethylaminoethyl methacrylate quaternized with dimethyl sulfate or with a dimethyl halide, such as that sold under the name Hercofloc by the company Hercules;

copolymers of acrylamide and of methacryloyloxyethyltrimethylammonium chloride which are disclosed, for example, in EP-A-080,976, the disclosure of which relating to cationic polymers is incorporated herein by reference, and sold, for example, under the name Bina Quat P 100 by the company Ciba-Geigy;

copolymers of acrylamide and of methacryloyloxyethyltrimethylammonium methosulfate, such as that sold under the name Reten by the company Hercules;

optionally quaternized vinylpyrrolidone/dialkyl-aminoalkyl (meth)acrylate copolymers, which are disclosed, for example, in French Patents 2,077,143 and 2,393,573, the disclosures of which relating to cationic polymers are incorporated herein by reference, and sold, for example, under the name "Gafquat" by the company ISP, such as, for example, "Gafquat 734" or "Gafquat 755", or else the products named "Copolymer 845, 958 and 937";

dimethylaminoethyl methacrylate/vinylcaprolactam/vinylpyrrolidone terpolymers, such as the product sold under the name Gaffix VC 713 by the company ISP, and the quaternized vinylpyrrolidone/dimethylamino-propylmethacrylamide copolymer, such as the product sold under the name "Gafquat HS 100" by the company ISP;

(2) the quaternized polysaccharides, disclosed more particularly in U.S. Pat. Nos. 3,589,578 and 4,031,307, the disclosures of which relating to quaternized polysaccharides polymers are incorporated herein by reference, such as guar gums comprising cationic trialkylammonium cationic groups.

Such products are sold in particular under the trade names Jaguar C13 S, Jaguar C 15, and Jaguar C 17 by the company Meyhall.

(3) quaternized copolymers of vinylpyrrolidone and of vinylimidazole, such as the products sold by BASF under the name Luviquat TFC.

(4) chitosans or their salts. The salts, which can be used, are in particular chitosan acetate, lactate, glutamate, gluconate, or pyrrolidone-carboxylate.

Mention may be made, among these compounds, of the chitosan having a degree of deacetylation of 90.5% by weight sold under the name Kytan Crude Standard by the company Aber Technologies and the chitosan pyrrolidone-carboxylate sold under-the name Kytamer PC by the company Amerchol.

(5) Cationic cellulose derivatives, such as the copolymers of cellulose or the cellulose derivatives grafted with a water-soluble quaternary ammonium monomer and disclosed in particular in U.S. Pat. No. 4,131,576, the disclosure of which relating to cationic cellulose derivatives is incorporated herein by reference. Examples include hydroxyalkyl celluloses, for example hydroxymethyl, hydroxyethyl, and hydroxypropyl celluloses grafted in particular with a methacryloylethyltrimethylammonium, methacrylamidopropyltrimethylammonium, or diallyldimethylammonium salt.

The commercial products corresponding to this definition are more particularly the products sold under the name "Celquat L 200" and "Celquat H 100" by the company National Starch.

The anionic fixing polymers, which can be used according to the present invention, are polymers comprising groups derived from carboxylic, sulphonic, and/or phosphoric acid and having a weight average molecular weight ranging from about 500 to about 5,000,000.

(1) The carboxyl groups may be contributed by unsaturated mono- or dicarboxylic acid monomers such as those corresponding to the formula:

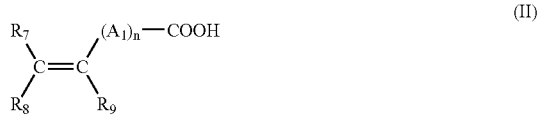

(II)

in which n is an integer ranging from 0 to 10; $A_1$ denotes a methylene group and when n is greater than 1, each $A_1$ is independently represented by -$LCH_2$-, where L is a valency bond or a heteroatom, such as oxygen or sulphur atom; $R_7$ is a radical chosen from hydrogen, phenyl groups, and benzyl groups; $R_8$ is a radical chosen from hydrogen, lower alkyl groups, and carboxyl groups; and $R_9$ is a radical chosen from hydrogen, lower alkyl groups, —$CH_2$—COOH groups, phenyl groups, and a benzyl groups.

In the above-mentioned formula, a lower alkyl radical denotes a group having 1 to 4 carbon atoms, such as methyl and ethyl.

The anionic fixing polymers comprising carboxyl groups according to the invention may be chosen from:

A) Homopolymers and copolymers of (meth)acrylic or (emth)acrylic salts and in particular the products sold under the names Versicol E or K by the company Allied Colloid and Ultrahold by the company BASF, the copolymers of acrylic acid and of acrylamide sold in the form of their sodium salt under the names Reten 421, 423, or 425 by the company Hercules, and the sodium salts of polyhydroxycarboxylic acids.

B) Copolymers of (meth)acrylic acid with a monoethylenic monomer, such as ethylene, styrene, vinyl esters, and (meth)acrylic acid esters, optionally grafted onto a polyalkylene glycol, such as polyethylene glycol, and optionally crosslinked. Such polymers are disclosed in particular in French Patent 1,222,944 and German Application 2,330,956, the disclosures of which relating to such copolymers are incorporated herein by reference. Tthe copolymers of this type comprising, in their chain, an optionally N-alkylated and/or hydroxyalkylated acrylamide unit, such as disclosed in particular in Luxembourg Patent Applications 75370 and 75371, the disclosures of which relating to such copolymers are incorporated herein by reference, or sold under the name Quadramer by the company American Cyanamid. Mention may also be made of copolymers of acrylic acid and of $C_1$–$C_4$ alkyl methacrylate and terpolymers of vinylpyrrolidone, of acrylic acid, and of $C_1$–$C_{20}$ alkyl methacrylate for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

C) copolymers derived from crotonic acid, such as those comprising, in their chain, vinyl acetate or propionate units and optionally other monomers, such as (meth)allyl esters, vinyl ether or vinyl ester of a linear or branched saturated carboxylic acid comprising a long hydrocarbon chain, such as those comprising at least 5 carbon atoms, it optionally being possible for these polymers to be grafted and crosslinked, or alternatively a vinyl, allyl, or methallyl ester of an α- or β-cyclic carboxylic acid. Such polymers are disclosed, inter alia, in French Patents 1,222,944, 1,580,545, 2,265,782, 2,265,781, 1,564,110, and 2,439,798, the disclosures of which relating to copolymers of crotonic acid are incorporated herein by reference. Commercial products coming within this class are the Resins 28-29-30, 26-13-14, and 28-13-10 sold by the company National Starch.

D) copolymers derived from $C_4$–$C_8$ monounsaturated carboxylic acids or anhydrides chosen from:

copolymers comprising units derived from (i) one or more maleic, fumaric, or itaconic acids or anhydrides and (ii) at least one monomer chosen from vinyl esters, vinyl ethers, vinyl halides, phenylvinyl derivatives, acrylic acids, and acrylic acid esters, the anhydride functional groups of these copolymers optionally being monoesterified or monoamidated. Such polymers are disclosed in particular in U.S. Pat. Nos. 2,047,398, 2,723,248, and 2,102,112 and GB 839,805, the disclosures of which relating to such copolymers are incorporated herein by reference, and in particular those sold under the names Gantrez AN or ES by the company ISP.

copolymers comprising units derived from (i) one or more maleic, citraconic, or itaconic anhydrides and (ii) one or more monomers chosen from (meth)allyl esters, optionally comprising one or more (meth)acrylamide, α-olefin, (meth)acrylic ester, (meth)acrylic acid, or vinylpyrrolidone groups in their chain. The anhydride functional groups of these copolymers optionally being monoesterified or monoamidated.

These polymers are, for example, disclosed in French Patents 2,350,384 and 2,357,241 the disclosures of which relating to such copolymers are incorporated herein by reference.

E) polyacrylamides comprising carboxylate groups.

(2) The anionic fixing polymers comprising sulfonic groups may be chosen from polymers comprising units, such as those derived from vinylsulphonic, styrenesulphonic, naphthalenesulphonic, and acrylamidoalkylsulphonic acids and their derivatives. These polymers may be chosen from:

salts of polyvinylsulphonic acid having a weight average molecular weight that ranges from about 1000 to about 100,000, as well as the copolymers with an unsaturated comonomer, such as acrylic and methacrylic acids, their esters, acrylamides, their derivatives, vinyl ethers, and vinylpyrrolidone;

salts of polystyrenesulphonic acid, the sodium salts having a weight average molecular weight ranging from about 100,000 to about 500,000, which are sold respectively under the names Flexan 500 and Flexan 130 by National Starch. These compounds are disclosed in Patent FR 2,198,719, the disclosure of which relating to salt of polystyrenesulphonic acid is incorporated herein by reference;

salts of polyacrylamidesulphonic acids, including those mentioned in U.S. Pat. No. 4,128,631, the disclosure of which relating to salt of polyacrylamidesulphonic acid is incorporated herein by reference, and more particularly the polyacrylamidoethylpropanesulphonic acid sold under the name Cosmedia Polymer HSP 1180 by Henkel.

In one embodiment, the anionic fixing polymers are chosen from acrylic acid copolymers, such as the acrylic acid/ethyl acrylate/N-tert-butylacrylamide terpolymer sold under the name Ultrahold Strong by the company BASF; copolymers derived from crotonic acid, such as the vinyl acetate/vinyl tert-butyl-benzoate/crotonic acid terpolymers and the crotonic acid/vinyl acetate/vinyl neododecanoate terpolymers sold under the name Resin 28-29-30 by the company National Starch; polymers derived from maleic, fumaric, or itaconic acids or anhydrides with vinyl esters, vinyl ethers, vinyl halides, phenylvinyl derivatives, or acrylic acid and its esters, such as the monoesterified methyl vinyl ether/maleic anhydride copolymer sold under the name Gantrez ES 425 by the company ISP; copolymers of methacrylic acid and of methyl methacrylate sold under the name Eudragit L by the company Rohm Pharma; the copolymer of methacrylic acid and of ethyl acrylate sold under the name Luvimer MAEX or MAE by the company BASF; the vinyl acetate/crotonic acid copolymer sold under the name Luviset CA 66 by the company BASF; and the vinyl acetate/crotonic acid copolymer grafted by polyethylene glycol sold under the name Aristoflex A by the company BASF.

In another embodiment, the anionic fixing polymers are chosen from the monoesterified methyl vinyl ether/maleic anhydride copolymer sold under the name Gantrez ES 425 by the company ISP; the acrylic acid/ethyl acrylate/N-tert-butylacrylamide terpolymer sold under the name Ultrahold Strong by the company BASF; the copolymers of methacrylic acid and of methyl methacrylate sold under the name Eudragit L by the company Rohm Pharma; the vinyl acetate/vinyl tert-butylbenzoate/crotonic acid terpolymers and the crotonic acid/vinyl acetate/vinyl neododecanoate terpolymers sold under the name Resin 28-29-30 by the company National Starch; the copolymer of methacrylic acid and of ethyl acrylate sold under the name Luvimer MAEX or MAE by the company BASF; and the vinyl-pyrrolidone/acrylic acid/lauryl methacrylate terpolymer sold under the name Acrylidone LM by the company ISP.

The amphoteric fixing polymers, which can be used in accordance with the invention, may be chosen from polymers comprising X and Y units, distributed randomly in the polymer chain, where the X unit is chosen from units derived from at least one monomer comprising at least one basic function, in particular a basic nitrogen atom, and where the Y unit is chosen from units derived from at least one acidic monomer comprising at least one group chosen from carboxyl groups and sulpho groups, or else where each X and Y unit is independently chosen from groups derived from zwitterionic carboxybetaine and sulphobetaine monomers. In another embodiment, the amphoteric fixing polymers, which can be used in accordance with the invention, may be chosen from polymers comprising X and Y units, each X and Y unit is independently chosen from at least one cationic polymer chain comprising at least one group chosen from primary amine groups, secondary amine groups, tertiary amine groups, and quaternary amine groups, in which at least one of the amine groups comprises a carboxyl or sulpho group linked by way of a hydrocarbon radical, or else the X and Y units, which may be different or identical, form part of a chain of at least one polymer comprising an α,β-dicarboxy ethylene unit, wherein at least one of the carboxyl groups has been reacted with a polyamine comprising at least one group chosen from primary and secondary amine groups.

In one embodiment, the amphoteric fixing polymers corresponding to the definition given above are chosen from the following polymers:

(1) polymers resulting from the copolymerization of a monomer derived from a vinyl compound carrying a carboxyl group, such as (meth)acrylic acids, maleic acids, and α-chloracrylic acids, and of a basic monomer derived from a substituted vinyl compound comprising at least one basic atom, such as dialkylaminoalkyl (meth)acrylate and dialkylaminoalkyl (meth)acrylamide. Such compounds are disclosed in U.S. Pat. No. 3,836,537, the disclosure of which relating to amphoteric polymers is incorporated herein by reference.

(2) polymers comprising units derived from:

a) at least one monomer chosen from (meth)acrylamides substituted on the nitrogen with an alkyl radical, b) at least one acidic comonomer comprising at least one reactive carboxylic group, and c) at least one basic comonomer, such as esters comprising primary, secondary, tertiary, and quaternary amine substituents of (meth)acrylic acids and the product of quaternization of dimethylaminoethyl methacrylate with dimethyl or diethyl sulfate.

The at least one (a) N-substituted (meth)acrylamides are more particularly chosen from N-substituted (meth)acrylamides, wherein the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide, and the corresponding methacrylamides.

The at least one (b) acidic comonomer is more particularly chosen from (meth)acrylic acids, crotonic acids, itaconic acids, maleic acids, fumaric acids, $C_1$–$C_4$ alkyl monoesters of maleic acid, $C_1$–$C_4$ alkyl monoesters of fumaric acid, $C_1$–$C_4$ alkyl monoesters of maleic anhydride, and $C_1$–$C_4$ alkyl monoesters of fumaric anhydride.

The at least one (c) basic comonomers is more particualry chosen from aminoethyl, butylaminoethyl, N,N'-dimethylaminoethyl, and N-tert-butylaminoethyl methacrylates.

In one embodiment, the amphoteric fixing polymer is chosen from the copolymers for which the CTFA name (4th Ed., 1991) is octylacrylamide/ acrylates/butylaminoethyl methacrylate copolymer, such as the products sold under the name Amphomer or Lovocryl 47 by the company National Starch.

(3) crosslinked and alkylated polyamino amides partially or totally derived from polyamino amides of general formula:

in which $R_{10}$ represents a divalent radical derived either from a saturated dicarboxylic acid, from an aliphatic mono- or dicarboxylic acid comprising an ethylenic double bond, from an ester of a lower alkanol having 1 to 6 carbon atom of these acids, or from a radical derived from the addition of any one of the said acids with a bisprimary or bissecondary amine; and Z denotes a radical of a bisprimary, mono- or bissecondary polyalkylenepolyamine and, for example, represents:

a) in the proportions of from about 60 mol % to 100 mol %, the radical:

where x=2 and p=2 or 3, or else x=3 and p=2 and where this radical derives from diethylenetriamine, triethylenetetraamine, or dipropylenetriamine;

b) in the proportions of from 0 mol % to about 40 mol %, the above radical (IV), in which x=2 and p=1 and which derives from ethylenediamine, or the radical derived from piperazine:

c) in the proportions of from 0 mol % to about 20 mol %, the —NH—$(CH_2)_6$—NH— radical derived from hexamethylenediamine, these polyamino amines being crosslinked by addition of a difunctional crosslinking agent chosen from epihalohydrines, diepoxides, dianhydrides and bis-unsaturated derivatives, using from about 0.025 mol to about 0.35 mol of crosslinking agent per amine group of the polyamino amide and alkylated by the action of acrylic acid, chloroacetic acid or an alkane sultone, or salts thereof.

In one embodiment, the saturated carboxylic acids are chosen from acids having 6 to 10 carbon atoms, such as adipic acid, 2,2,4-trimethyladipic acid, 2,4,4-trimethyladipic acid, terephthalic acid, and acids comprising an ethylenic double bond such as, for example, acrylic acid, methacrylic acid and itaconic acid.

In one embodiment, the alkane sultones used in the alkylation are chosen from propane sultone and butane sultone and the salts of the alkylating agents are chosen from sodium and potassium salts.

(4) polymers comprising zwitterionic units of formula:

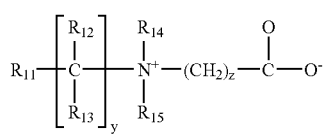

in which $R_{11}$, is chosen from polymerizable unsaturated groups such as an (meth)acrylate and (meth)acrylamide groups; y and z are independently chosen from integers ranging from 1 to 3; $R_{12}$ and $R_{13}$ are independently chosen from hydrogen, methyl groups, ethyl groups, and propyl groups; $R_{14}$ and $R_{15}$ are independently chosen from hydrogen and alkyl radicals, wherein the sum of the carbon atoms in $R_{14}$ and $R_{15}$ is less than or equal to 10.

The polymers comprising such units may further comprise units derived from non-zwitterionic monomers, such as dimethylaminoethyl (meth)acrylate, diethylaminoethyl (meth)acrylate, alkyl (meth)acrylates, (meth)acrylamides, and vinyl acetates.

Mention may be made, by way of example, of the methyl methacrylate/ methyl dimethylcarboxymethylammonioethyl methacrylate copolymer, such as the product sold under the name Diaformer Z301 by the company Sandoz.

(5) polymers derived from chitosan comprising monomer units corresponding to the following formulae:

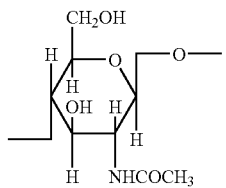

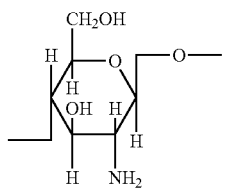

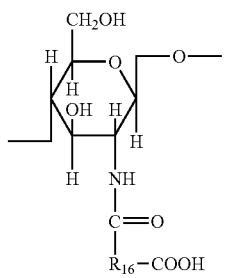

the unit D being present in proportions ranging from 0% to about 30%, the unit E in proportions ranging from about 5% to about 50% and the unit F in proportions ranging from about 30% to about 90%, it being understood that, in this unit F, $R_{16}$ represents a radical of formula:

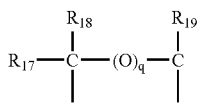

in which, if q=0, $R_{17}$, $R_{18}$, and $R_{19}$, which are identical or different, are chosen from hydrogen, methyl groups, hydroxyl groups, acetoxy groups, amino residues, monoalkylamine residues, and dialkylamine residues, optionally interrupted by one or more nitrogen atoms and/or optionally substituted by one or more amine, hydroxyl, carboxy, alkylthio, or sulpho groups, and alkylthio residues in which the alkyl group carries an amino residue, at least one of the $R_{17}$, $R_{18}$, and $R_{19}$ radicals being, in this case, hydrogen; or, if q=1, $R_{17}$, $R_{18}$, and $R_{19}$ each represent hydrogen, and the salts formed by these compounds with bases or acids.

(6) Polymers derived from the N-carboxyalkylation of chitosan, such as the N-(carboxymethyl)chitosan or the N-(carboxybutyl)chitosan sold under the name "Evalsan" by the company Jan Dekker.

(7) Polymers corresponding to the general formula (VI), for example disclosed in French Patent 1,400,366, the disclosure of which relating to amphoteric polymers is incorporated herein by reference:

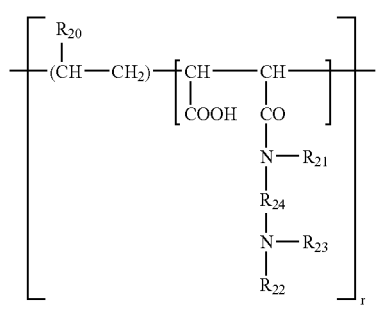

in which $R_{20}$ is a radical chosen from hydrogen, $CH_3O$, $CH_3CH_2O$, and phenyl radicals; $R_{21}$ is chosen from hydrogen and lower alkyl radicals such as methyl or ethyl; $R_{22}$ is chosen from hydrogen and lower alkyl radicals such as methyl or ethyl; and $R_{23}$ is chosen from lower alkyl radicals such as methyl or ethyl and radicals corresponding to the formula: —$R_{24}$—$N(R_{22})_2$, where $R_{24}$ represents a —$CH_2$—$CH_2$—, —$CH_2$—$CH_2$—$CH_2$—, or —$CH_2$—$CH(CH_3)$— group and $R_{22}$ is the same as above, and the higher homologues of these radicals comprising up to 6 carbon atoms.

(8) Amphoteric fixing polymers of the -D-X-D-X- type chosen from:

a) polymers obtained by reaction of chloracetic acid or sodium chloracetate with compounds comprising at least one unit of formula:

$$\text{-D-X-D-X-D-} \quad (VII)$$

where D denotes a radical

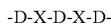

and X denotes the symbol E or E'. E and E', which are identical or different, denote a divalent radical chosen from straight- and branched-chain alkylene radicals comprising up to 7 carbon atoms in the main chain, which, is unsubstituted or substituted by hydroxyl groups and which can additionally comprise oxygen, nitrogen, or sulphur atoms or 1 to 3 aromatic and/or heterocyclic rings; the oxygen, nitrogen, and sulphur atoms being present in the form of ether, thioether, sulphoxide, sulphone, sulphonium, alkylamine or alkenylamine groups, benzylamine, amine oxide, quaternary ammonium, amide, imide, alcohol, ester, and/or urethane groups.

b) Polymers of formula:

$$\text{-D-X-D-X-} \quad (VII')$$

in which D denotes a radical

and X denotes the symbol E or E' and E' at least once, where E has the meaning indicated above and E' is a divalent radical chosen from straight- and branched-chain alkylene radicals having up to 7 carbon atoms in the main chain, which is substituted or unsubstituted by one or more hydroxyl radicals and which comprises one or more nitrogen atoms, the nitrogen atom being substituted by an alkyl chain optionally interrupted by an oxygen atom and necessarily comprising one or more carboxyl functional groups or one or more hydroxyl functional groups and wherein the polymer of formula VII' is betainized by reaction with chloracetic acid or sodium chloracetate.

(9) $(C_1–C_5)$alkyl vinyl ether/maleic anhydride copolymers, which are partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

In one embodiment, the amphoteric fixing polymers according to the invention are chosen from family (3), such as the copolymers with the CTFA name ($4^{th}$ Ed. 1991) of octylacrylamide/acrylates/butylaminoethyl methacrylate copolymer, such as the products sold under the names Amphomer, Amhomer LV 71, or Lovocryl 47 by the company National Starch, and family (4), such as the copolymer of methyl methacrylate/dimethyl carboxymethylammonio methyl ethylmethacrylate, sold, for example, under the name Diaformer Z301 by the company Sandoz.

The nonionic fixing polymers, which can be used according to the present invention, are chosen, for example, from:
vinylpyrrolidone homopolymers;
copolymers of vinylpyrrolidone and of vinyl acetate;
polyalkyloxazolines, such as the polyethyloxazolines sold by the company Dow Chemical under the names PEOX 50 000, PEOX 200 000 and PEOX 500 000;
vinyl acetate homopolymers, such as the product sold under the name Appretan EM by the company Hoechst or the product soldd under the name Rhodopas A 012 by the company Rhone-Poulenc;
copolymers of vinyl acetate and of acrylic ester, such as the product sold under the name Rhodopas AD 310 by Rhône-Poulenc;
copolymers of vinyl acetate and of ethylene, such as the product sold under the name Appretan TV by the company Hoechst;
copolymers of vinyl acetate and of maleic ester, for example of dibutyl maleate, such as the product sold under the name Appretan MB Extra by the company Hoechst;
copolymers of polyethylene and of maleic anhydride;
alkyl acrylate homopolymers and alkyl methacrylate homopolymers, such as the product sold under the name Micropearl RQ 750 by the company Matsumoto or the product sold under the name Luhydran A 848 S by the company BASF;
acrylic ester copolymers such as, for example, copolymers of alkyl (meth)acrylates, such as the products sold by the company Rohm & Haas under the names Primal AC-261 K and Eudragit NE 30 D, by the company BASF under the names Acronal 601, Luhydran LR 8833 or 8845, and by the company Hoechst under the names Appretan N 9213 or N 9212;
copolymers of acrylonitrile and of a nonionic monomer chosen, for example, from butadiene and alkyl (meth)acrylates; mention may be made of the products sold under the names Nipol LX 531 B by the company Nippon Zeon or those sold under the name CJ 0601 B by the company Rohm & Haas;

polyurethanes, such as the products sold under the names Acrysol RM 1020 or Acrysol RM 2020 by the company Rohm & Haas, and the products Uraflex XP 401 UZ and Uraflex XP 402 UZ by the company DSM Resins;

copolymers of alkyl acrylate and of urethane, such as the product 8538-33 by the company National Starch;

polyamides, such as the product Estapor LO 11 sold by the company Rhône-Poulenc.

nonionic guar gums that are chemically modified or unmodified.

The unmodified nonionic guar gums are, for example, the products sold under the name Vidogum GH 175 by the company Unipectine and under the name Jaguar C by the company Meyhall.

The modified nonionic guar gums, which may be used according to the invention, are, for example, modified with $C_1$–$C_6$ hydroxyalkyl groups. Examples, which may be mentioned, are hydroxymethyl, hydroxyethyl, hydroxypropyl and hydroxybutyl groups.

These guar gums are well known in the prior art and may be prepared, for example, by reacting corresponding alkene oxides such as, for example, propylene oxides with guar gum so as to obtain a guar gum modified with hydroxypropyl groups.

Such nonionic guar gums, optionally modified with hydroxyalkyl groups, are sold, for example, under the trade names Jaguar HP8, Jaguar HP60, Jaguar HP120, Jaguar DC 293 and Jaguar HP 105 by the company Meyhall and under the name Galactosol 4H4FD2 by the company Aqualon.

The alkyl radicals in the nonionic polymers comprise from 1 to 6 carbon atoms, except where otherwise mentioned.

According to the invention, it is also possible to use fixing polymers of grafted silicone type comprising a polysiloxane portion and a portion composed of a non-silicone organic chain, one of the two portions constituting the main chain of the polymer and the other being grafted onto the said main chain. These polymers are disclosed, for example, in EP-A-0,412,704, EP-A-0,412,707, EP-A-0,640,105, WO 95/00578, EP-A-0,582,152, and WO 93/23009 and U.S. Pat. Nos. 4,693,935, 4,728,571, and 4,972,037, the disclosures of which relating to grafted silicone type polymers are incorporated herein by reference. These polymers are, for example, anionic or nonionic.

Such polymers are, for example, copolymers which can be obtained by radical polymerization from the monomer mixture comprising:

a) about 50% to about 90% by weight of tert-butyl acrylate;
b) 0% to about 40% by weight of acrylic acid;
c) about 5% to about 40% by weight of silicone macromer of formula:

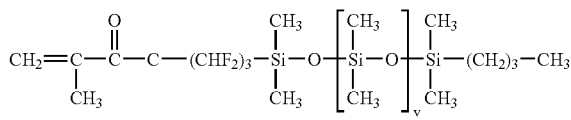

where v is a number ranging from 5 to 700; the percentages by weight being calculated with respect to the total weight of the monomers.

Other examples of grafted silicone polymers are, in particular, polydimethylsiloxanes (PDMSs) onto which are grafted, via a thiopropylene-type connecting chain, mixed polymer units of the poly(meth)acrylic acid type and of the poly(alkyl (meth)acrylate) type and polydimethylsiloxanes (PDMSs) onto which are grafted, via a thiopropylene-type connecting chain, polymer units of the poly(isobutyl (meth) acrylate) type.

It is also possible to use, as fixing polymers, functionalized or non-functionalized and silicone-comprising or non-silicone-comprising polyurethanes.

The polyurethanes particularly targeted by the present invention are those disclosed in Patents EP 0,751,162, EP 0,637,600, FR 2,743,297, EP 0,648,485, EP 0,656,021, WO 94/03510, and EP 0,619,111, the disclosure of which relating to poylurethanes are incorporated herein by reference.

In a further embodiment, the fixing polymers may be used in solubilized form or may be in the form of dispersions of solid particles (latex or pseudo-latex).

The compositions according to the invention can be provided in any form known from the prior art, which is appropriate for their application to the hair, including in the form of a vaporizable composition such as sprays and aerosols, mousse, gel, stick, mud, or lotion.

The composition may be in any of the conventional forms of cosmetic composition including, but not limited to, shampoos, hair rinses, permanent waving compositions, waving compositions, hair dye compositions, hair straightening compositions, hair fixing products, hair styling gel products, products to use before or after a hair dye treatment, products to use before or after a permanent waving treatment, hair straightening compositions, products to use before or after a hair straightening treatment, and fixing foams.

The composition according to the invention may be vaporizable, for example by a pump, or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term lower alcohol means a $C_1$ to $C_4$ aliphatic alcohol, such as ethanol.

When the vaporizable composition according to the invention is an aerosol composition, it additionally comprises an appropriate amount of propellant. The propellant comprises compressed or liquefied gases, which are normally employed for the preparation of aerosol compositions. Suitable gasses include compressed air, carbon dioxide, nitrogen, and gases, which may be soluble in the composition, such as dimethyl ether, fluorinated or non-fluorinated hydrocarbons, and mixtures thereof.

The present invention additionally provides an aerosol device comprising a vessel comprising an aerosol composition, which comprises a liquid phase (or juice) comprising at least one hair styling material, as described above, in an appropriate medium and a propellant, and a dispenser, such as a dispensing valve, for dispensing said aerosol composition from the vessel.

The present invention additionally provides a method of treating keratinous fibers, especially hair, in which the composition according to the invention, as described above, is applied to the hair before, during, or after the shaping of the hairstyle.

The compositions according to the invention can be rinsed off or not rinsed off the hair.

The present invention additionally provides the use of a composition as described above in, or for the preparation of, a cosmetic reshapable hair styling formulation.

The determination of whether a composition with a (meth)acrylic copolymer according to the invention can provide a reshapable effect can be determined by an in vivo test.

Where the composition is in the form of a lotion, for example, the in vivo test proceeds as follows. The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cosmetic properties, and the reshapable effect. For example, once dried, the hair is brushed in different directions to remove the original styling. The hair is then brushed to restore the original styling. The process of removing the styling, restoring the styling, and evaluating the success of restoring the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10–20 different individuals.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The invention may be understood more clearly with the aid of the non-limiting examples that follow, and which constitute an advantageous embodiment of the compositions in accordance with the invention.

EXAMPLES

Hair compositions according to the invention, as well as comparative compositions, were produced with different (meth)acrylic copolymers. Percentages given are by weight, unless otherwise specified.

1) Preparation of the (Meth)acrylic Copolymers

Example 1 (Tetrapolymer Made by Semi-Continuous Emulsion Polymerization)

A solution of 1.0 grams carbon tetrabromide was prepared in a mixture of 275 grams 2-ethyl hexyl acrylate (2-E HA), 200 grams isobornyl acrylate (IBOA), 12.5 grams methacrylic acid (MAA), and 12.5 grams acrylic acid (AA) yielding 500 grams of a monomer solution containing 55/40/2.5/2.5 parts 2-EHA/IBOA/MAA/AA. Of the total monomer solution, 50 grams was charged into a two liter split resin flask along with 390 grams of deionized water and 0.5 gram of sodium dodecyl benzene sulfonate. The head was placed on the flask and a thermocouple, nitrogen inlet, and mechanical stirrer attached. The contents were heated with infrared lamps to about 60° C. while stirring at 350 rpm. A solution of 1.25 grams potassium persulfate in 20 grams deionized water was charged, the flask sealed, and a vacuum pulled on the flask four times, breaking it each time with nitrogen. The flask was held at 60° C. for 20 minutes, then heated to 80° C. over 10 minutes to yield a seed polymer. A pre-emulsion of the remaining 450 grams of the monomer solution was prepared by charging a solution of 4.5 grams of sodium dodecyl benzene sulfonate in 201 grams of deionized water to it and stirring under nitrogen. This pre-emulsion was added dropwise to the two liter split resin flask containing the seed polymer at a rate of 6 grams per minute. The addition took almost 2 hours. After the addition, the stirring rate was reduced to 200 rpm and the reaction held at 80° C. for two hours, then the resulting latex was filtered through doubled over cheesecloth into a jar. Low levels of coagulum were noted around the thermocouple and stirring paddle.

Example 2 (Tetrapolymer may be Made by Batch Emulsion Polymerization)

Into a one liter Mortonized split resin flask may be charged 100 grams of monomers (45 grams 2-EHA, 35 grams IBOA, 10 grams MAA, and 10 grams AA), 80 milligrams of carbon tetrabromide, 124.7 grams of deionized water, 200 milligrams of potassium persulfate, 64 milligrams of sodium metabisulfite, 1 gram of sodium dodecyl benzene sulfonate, and 2.5 grams of Mazon SAM 211 alkylene polyalkoxy ammonium sulfate copolymerizable surfactant (available from PPG Industries, Pittsburgh, Pa.). The head is placed on the flask and a thermocouple, nitrogen inlet, and mechanical stirrer are attached. The headspace is swept with nitrogen at 1 liter per minute while heating the contents with infrared lamps to about 30° C. and stirring at 250 rpm. About 1 gram of a solution of 28 milligrams ferrous sulfate heptahydrate in 50 grams deionized water is charged, the flask sealed, and a vacuum pulled on the flask three times, breaking it each time with nitrogen. After 15 or 20 minutes an exotherm is noted which peaks 20 to 25 minutes later at 55° C. to 65° C. Reactor temperature is increased to about 75° C. and held for one hour, then the resulting latex is-filtered through doubled over cheesecloth into a jar.

Example 3 (Tetrapolymer may be Made by Solution Polymerization and Inversion in Water)

Into a 120 milliliter glass bottle may be charged with 24 grams of monomers (8.4 grams 2-EHA, 13.2 grams cyclohexyl methacrylate (CHXMA), 1.2 grams MAA, and 1.2 grams AA), 120 milligrams of carbon tetrabromide, 36 grams of methylethyl ketone, and 72 milligrams of azobis (isobutyronitrile). The contents of the bottle are swept with nitrogen at about 1 liter per minute for two minutes, then the bottle is capped and tumbled in a water bath for 24 hours at about 55° C. to yield a moderate viscosity solution. 15 grams (containing 6 grams of polymer or 8.3 milliequivalents of carboxylic acid) of the resulting solution is charged into a 250 milliliter round bottom flask containing a solution of 0.67 grams (7.5 milliequivalents, 90% neutralization) of 2-amino-2-methyl-1-propanol in 14 grams of deionized water with moderate agitation. The solvent is removed from the resulting dispersion by a rotary evaporator set at about 63° C. at a reduced pressure of 40 kilopascals to yield a milky white dispersion.

Example 4 (Pentapolymer may be Made by Suspension Polymerization)

In a one liter Mortonized split resin flask may be charged 240 gram of a monomer mixture (120 grams 2-EHA, 54 grams IBOA, 54 grams (CHXMA), 6 grams MAA, and 6 grams AA). Added to the flask is 6.9 grams Ludox™ 50 (50% by wt colloidal silica in water, available from Aldrich, Milwaukee, Wis.), 360 grams deionized water, 0.42 grams adipic acid/diethanol amine condensate (a 50% solids used as a promoter, is prepared according to the procedure disclosed in U.S. Pat. No. 5,238,736), and 0.08 grams potassium dichromate. The head is placed on the flask and a thermocouple, nitrogen inlet, and mechanical stirrer are attached. The entire content inside the flask is mixed. The pH is measured and adjusted by adding ammonium hydroxide to a pH between 4 and 5. The mixture is then transferred to a Waring™ blender and exposed to high shear (about 22,000 rpm) for six minutes total, using shear for about two minutes at a time to avoid overheating the mixture.

The mixture is then returned to the Mortonized flask and 0.36 grams of Vazo™ 64 (azo-bis(isobutyronitrile) initiator, available from E.I. du Pont de Nemours & Co., Wilmington, Del.) is added. A nitrogen purge is started and the mixture is agitated gently for several minutes to let the initiator dissolve. The agitation speed is adjusted to about 300 rpm and the temperature is set at about 60° C. The reaction is started within minutes and is allowed to exotherm. After exotherming, the temperature is maintained at about 60° C. for about four hours.

Example 5

A 50/50 mixture of the emulsion from Example 1 and a dispersion comprising AQ 1350 by the Eastman Chemical Co. as disclosed in WO 98/38969 may be made.

Example 6

A 25/75 mixture of the emulsion from Example 1 and the emulsion from Example 2 may be made.

2) Preparation of Comparative Terpolymers

Comparative Examples A and B (Terpolymers Made by Batch Emulsion Polymerization)

Into a one liter Mortonized split resin flask was charged 100 grams of monomers (detailed in Table I below), 80 milligrams of carbon tetrabromide, 124.7 grams of deionized water, 200 milligrams of potassium persulfate, 64 milligrams of sodium metabisulfite, 1 gram of sodium dodecyl benzene sulfonate, and 2.5 grams of Mazon SAM 211 alkylene polyalkoxy ammonium sulfate copolymerizable surfactant (available from PPG Industries, Pittsburgh, Pa.). The head was placed on the flask and a thermocouple, nitrogen inlet, and mechanical stirrer attached. The headspace was swept with nitrogen at 1 liter per minute while heating the contents with infrared lamps to about 30° C. and stirring at 250 rpm. About 1 gram of a solution of 28 milligrams ferrous sulfate heptahydrate in 50 grams deionized water was charged, the flask sealed, and a vacuum pulled on the flask three times, breaking it each time with nitrogen. After 15 or 20 minutes an exotherm is noted which peaks 20 to 25 minutes later at 55° C. to 65° C. Reactor temperature is increased to about 75° C. and held for one hour, then the resulting latex was filtered through doubled over cheesecloth into a jar. In all cases moderate levels of coagulum were noted around the thermocouple and stirring paddle.

TABLE I

Monomer Charges Used for Batch Emulsion Polymerization

| Example | g 2-EHA | g IBOA | g AA | g MAA |
|---------|---------|--------|------|-------|
| A | 60 | 35 | 0 | 5 |
| B | 50 | 45 | 5 | 0 |

2-EHA = 2-ethylhexyl acrylate
IBOA = isobornyl acrylate
AA = acrylic acid
MAA = methacrylic acid 3) Preparation of the Hair Styling Compositions One comparative hair styling composition not in accordance with the invention and one hair styling composition in accordance with the invention were prepared using the components and amounts in weight percent listed hereafter. The testing was conducted on several models with one part of the head receiving a reference composition and the other side of the head receiving the tested composition. The compositions were applied to wet hair after shampooing. The hair was then dried, brushed, and evaluated.

| Reference 1: | |
|---|---|
| AQ 1350 | 4% active material |
| Water | qsp 100% |
| Reference 2 | |
| Comparative Example A | 2% active material |
| Comparative Example B | 2% active material |
| Water | qsp 100% |

-continued

| Formulation A (comparative) | |
|---|---|
| Comparative Example A | 2% active material |
| Comparative Example B | 2% active material |
| Water | qsp 100% |

Formulation A imparted very good hairstyling and a very good reshapable effect with correct cosmetic properties, as compared with Reference 1.

Note: Both Formulation A (comparative) and Reference 2 comprise Comparative Examples A and B polymers; however, the polymers were from separate batches.

| Formulation B: | |
|---|---|
| Example 1 | 4% active material |
| Water | qsp 100% |

Formulation B imparted very good hairstyling and a very good reshapable effect with average cosmetic properties, such as untangling, volume, and feel, as compared with Reference 2. Shine was somewhat better, while softness and body were not optimum, as compared to the reference. Thus, the tetrapolymer (55/40/2.5/2.5 parts 2-EHA/IBOA/MAA/AA) may yield a better reshapable effect than a comparable blend (60/35/5 parts 2-EHA/IBOA/MAA with 50/45/5 parts 2-EHA/IBOA/AA, having a net composition of 55/40/2.5/2.5 parts 2-EHA/IBOA/MAA/AA).

What is claimed is:

1. A reshapable hair styling composition comprising at least one (meth)acrylic copolymer comprising:
    (a) units derived from at least one monomer chosen from (meth)acrylate esters of branched and straight chain alkyl alcohols,
    (b) units derived from at least one monomer chosen from (meth)acrylate esters of saturated and unsaturated cyclic alcohols containing 6 to 20 carbon atoms,
    (c) optional units derived from at least one monomer chosen from hydrophilic monomers, and
    (d) optional units derived from at least one monomer other than said (a), (b), and (c) monomers,
    wherein said at least one (meth)acrylic copolymer comprises units derived from at least four different monomers; and
    wherein said composition provides a reshapable effect, wherein said reshapable effect provides a hair styling that can be modified without adding new material or heat being applied.

2. The composition according to claim 1, wherein the composition further comprises a cosmetically acceptable vehicle.

3. The composition according to claim 1, wherein said at least one monomer recited in (a) is chosen from (meth)acrylate esters of $C_1$ to $C_{30}$ branched and straight chain alkyl alcohols.

4. The composition according to claim 1, wherein said at least one monomer recited in (a) is chosen from (meth)acrylate esters of $C_4$ to $C_{18}$ branched and straight chain alkyl alcohols.

5. The composition according to claim 1, wherein said at least one monomer recited in (a) is chosen from isooctyl (meth)acrylate, n-butyl (meth)acrylate, isobutyl (meth)acrylate, t-butyl (meth)acrylate, 2-methylbutyl (meth)acrylate, 2-ethylhexyl (meth)acrylate, n-octyl (meth)acrylate, isononyl (meth)acrylate, lauryl (meth)acrylate, and octadecyl (meth)acrylate.

6. The composition according to claim 1, wherein said at least one monomer recited in (b) is chosen from bicyclo[2.2.1]heptyl (meth)acrylate, adamantyl (meth)acrylate, 3,5-dimethyladamantyl (meth)acrylate, isobornyl (meth)acrylate, tolyl (meth)acrylate, phenyl (meth)acrylate, t-butylphenyl (meth)acrylate, 2-napthyl (meth)acrylate, benzyl (meth)acrylate, cyclohexyl (meth)acrylate, menthyl (meth)acrylate, 3,3,5-trimethylcyclohexyl (meth)acrylate, dicyclopentenyl (meth)acrylate, and 2-(dicyclopentenyloxy)ethyl (meth)acrylate.

7. The composition according to claim 1, wherein said at least one monomer recited in (c) is chosen from (meth)acrylic acid and N-vinyl-2-pyrrolidone.

8. The composition according to claim 1, wherein said at least one monomer recited in (d) is chosen from vinyl esters, vinyl chlorides, vinylidene chlorides, styrenes, (meth)acrylate esters of $C_1$ to $C_3$ alkyl alcohols, monoacrylic functional polystyrene, and polydimethylsiloxane.

9. The composition according to claim 1, wherein said at least one (meth)acrylic copolymer is present in an amount ranging from about 0.1 to about 40 weight percent of the total weight percent of the composition.

10. The composition according to claim 9, wherein the amount of said at least one (meth)acrylic copolymer ranges from about 0.5 to about 15 weight percent.

11. The composition according to claim 1, wherein said at least one (meth)acrylic copolymer has a Tg ranging from about $-100°$ C. to about $150°$ C.

12. The composition according to claim 1, wherein the composition further comprises at least one additional polymer.

13. The composition according to claim 12, wherein said at least one additional polymer is chosen from anionic, cationic, amphoteric, and nonionic polymers.

14. The composition according to claim 1, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

15. A reshapable hair styling composition comprising at least one (meth)acrylic copolymer comprising:
    (a) units derived from at least one monomer chosen from (meth)acrylate esters of branched and straight chain alkyl alcohols,
    (b) units derived from at least one monomer chosen from (meth)acrylate esters of saturated and unsaturated cyclic alcohols containing 6 to 20 carbon atoms,
    (c) optional units derived from at least one monomer chosen from hydrophilic monomers, and
    (d) optional units derived from at least one monomer other than said (a), (b), and (c) monomers,
    wherein said at least one (meth)acrylic copolymer comprises units derived from at least four different monomers,
    wherein said composition provides a reshapable effect and is in the form of a spray, aerosol, mousse, gel, stick, mud, or lotions, wherein said reshapable effect provides a hair styling that can be restored or modified without adding new material or heat being applied.

16. An aerosol device comprising a vessel, which comprises:
(1) an aerosol composition, which provides a reshapable effect and comprises a liquid phase comprising at least one composition comprising at least one (meth)acrylic copolymer comprising:
   (a) units derived from at least one monomer chosen from (meth)acrylate esters of branched and straight chain alkyl alcohols,
   (b) units derived from at least one monomer chosen from (meth)acrylate esters of saturated and unsaturated cyclic alcohols containing 6 to 20 carbon atoms,
   (c) optional units derived from at least one monomer chosen from hydrophilic monomers, and
   (d) optional units derived from at least one monomer other than said (a), (b), and (c) monomers,
   wherein said at least one (meth)acrylic copolymer comprises units derived from at least four different monomers; and
   wherein said composition provides a reshapable effect and a propellant,
   wherein said reshapable effect provides a hair styling that can be modified without adding new material or heat being applied and
(2) a dispenser.

17. A method of cosmetically treating hair, comprising applying to the hair before, during, or after shaping of a hairstyle of said hair a composition comprising at least one (meth)acrylic copolymer comprising:
   (a) units derived from at least one monomer chosen from (meth)acrylate esters of branched and straight chain alkyl alcohols,
   (b) units derived from at least one monomer chosen from (meth)acrylate esters of saturated and unsaturated cyclic alcohols containing 6 to 20 carbon atoms,
   (c) optional units derived from at least one monomer chosen from hydrophilic monomers, and
   (d) optional units derived from at least one monomer other than said (a), (b), and (c) monomers,
   wherein said at least one (meth)acrylic copolymer comprises units derived from at least four different monomers; and
   wherein said composition provides a reshapable effect,
   wherein said reshapable effect provides a hair styling that can be modified without adding new material or heat being applied.

18. A method of reshaping hair, comprising:
(1) applying to the hair before, during, or after the initial shaping of the hairstyle a composition comprising at least one (meth)acrylic copolymer comprising:
   (a) units derived from at least one monomer chosen from (meth)acrylate esters of branched and straight chain alkyl alcohols,
   (b) units derived from at least one monomer chosen from (meth)acrylate esters of saturated and unsaturated cyclic alcohols containing 6 to 20 carbon atoms,
   (c) optional units derived from at least one monomer chosen from hydrophilic monomers, and
   (d) optional units derived from at least one monomer other than said (a), (b), and (c) monomers,
   wherein said at least one (meth)acrylic copolymer comprises units derived from at least four different monomers; and
   wherein said composition provides a reshapable effect,
   wherein said reshapable effect provides a hair styling that can be modified without adding new material or heat being applied, and
(2) thereafter shaping the hairstyle at least once, wherein no additional composition or heat is added.

19. A method of manufacturing a reshapable hair styling composition comprising including in a hair styling composition at least one (meth)acrylic copolymer comprising:
   (a) units derived from at least one monomer chosen from (meth)acrylate esters of branched and straight chain alkyl alcohols,
   (b) units derived from at least one monomer chosen from (meth)acrylate esters of saturated and unsaturated cyclic alcohols containing 6 to 20 carbon atoms,
   (c) optional units derived from at least one monomer chosen from hydrophilic monomers, and
   (d) optional units derived from at least one monomer other than said (a), (b), and (c) monomers,
   wherein said at least one (meth)acrylic copolymer comprises units derived from at least four different monomers; and
   wherein said at least one (meth)acrylic copolymer is present in an amount effective to provide a reshapable effect,
   wherein said reshapable effect provides a hair styling that can be modified without adding new material or heat being applied.

20. A reshapable hair styling composition comprising at least one (meth)acrylic copolymer comprising:
   (a) from about 10 to about 85 weight percent of units derived from at least one monomer chosen from (meth)acrylate esters of branched and straight chain alkyl alcohols,
   (b) from about 5 to about 70 weight percent of units derived from at least one monomer chosen from (meth)acrylate esters of saturated and unsaturated cyclic alcohols containing 6 to 20 carbon atoms,
   (c) from 0 to about 20 weight percent of units derived from at least one monomer chosen from hydrophilic monomers, and
   (d) from 0 to about 20 weight percent of units derived from at least one monomer other than said (a), (b), and (c) monomers,
   wherein said at least one (meth)acrylic copolymer comprises units derived from at least four different monomers; and
   wherein said composition provides a reshapable effect,
   wherein said reshapable effect provides a hair styling that can be modified without adding new material or heat being applied.

21. The composition according to claim 20, wherein the composition further comprises a cosmetically acceptable vehicle.

22. The composition according to claim 20, wherein said at least one monomer recited in (a) is chosen from (meth)acrylate esters of $C_1$ to $C_{30}$ branched and straight chain alkyl alcohols.

23. The composition according to claim 20, wherein said at least one monomer recited in (a) is chosen from (meth)acrylate esters of $C_4$ to $C_{18}$ branched and straight chain alkyl alcohols.

24. The composition according to claim 20, wherein said at least one monomer recited in (a) is chosen from isooctyl (meth)acrylate, n-butyl (meth)acrylate, isobutyl (meth)acrylate, t-butyl (meth)acrylate, 2-methylbutyl (meth)acrylate, 2-ethylhexyl (meth)acrylate, n-octyl (meth)acrylate, isononyl (meth)acrylate, lauryl(meth)acrylate, and octadecyl (meth)acrylate.

25. The composition according to claim 20, wherein said at least one monomer recited in (b) is chosen from bicyclo [2.2.1]heptyl (meth)acrylate, adamantyl (meth)acrylate, 3,5-dimethyladamantyl (meth)acrylate, isobornyl (meth)acrylate, tolyl (meth)acrylate, phenyl (meth)acrylate, t-butylphenyl (meth)acrylate, 2-napthyl (meth)acrylate, benzyl (meth)acrylate, cyclohexyl (meth)acrylate, menthyl (meth)acrylate, 3,3,5-trimethylcyclohexyl (meth)acrylate, dicyclopentenyl (meth)acrylate, and 2-(dicyclopentenyloxy) ethyl (meth)acrylate.

26. The composition according to claim 20, wherein said at least one monomer recited in (c) is chosen from (meth) acrylic acid and N-vinyl-2-pyrrolidone.

27. The composition according to claim 20, wherein said at least one monomer recited in (d) is chosen from vinyl esters, vinyl chlorides, vinylidene chlorides, styrenes, (meth)acrylate esters of $C_1$ to $C_3$ alkyl alcohols, monoacrylic functional polystyrene, and polydimethylsiloxane.

28. The composition according to claim 20, wherein said at least one (meth)acrylic copolymer is present in an amount ranging from about 0.1 to about 40 weight percent of the total weight percent of the composition.

29. The composition according to claim 28, wherein the amount of said at least one (meth)acrylic copolymer ranges from about 0.5 to about 15 weight percent.

30. The composition according to claim 20, wherein said at least one (meth)acrylic copolymer has a Tg ranging from about −100° C. to about 15° C.

31. The composition according to claim 20, wherein the composition further comprises at least one additional polymer.

32. The composition according to claim 31, wherein said at least one additional polymer is chosen from anionic, cationic, amphoteric, and nonionic polymers.

33. The composition according to claim 20, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

34. A reshapable hair styling composition comprising at least one (meth)acrylic copolymer comprising:
 (a) from about 10 to about 85 weight percent of units derived from at least one monomer chosen from (meth) acrylate esters of branched and straight chain alkyl alcohols,
 (b) from about 5 to about 70 weight percent of units derived from at least one monomer chosen from (meth) acrylate esters of saturated and unsaturated cyclic alcohols containing 6 to 20 carbon atoms,
 (c) from 0 to about 20 weight percent of units derived from at least one monomer chosen from hydrophilic monomers, and
 (d) from 0 to about 20 weight percent of units derived from at least one monomer other than said (a), (b), and (c) monomers,
 wherein said at least one (meth)acrylic copolymer comprises units derived from at least four different monomers; and
 wherein said composition provides a reshapable effect and is in the form of a spray, aerosol, mousse, gel, stick, mud, or lotion,
 wherein said reshapable effect provides a hair styling that can be restored or modified without new material or heat being applied.

35. An aerosol device comprising a vessel, which comprises:
 (1) an aerosol composition, which provides a reshapable effect and comprises a liquid phase comprising at least one composition comprising at least one (meth)acrylic copolymer comprising:
  (a) from about 10 to about 85 weight percent of units derived from at least one monomer chosen from (meth)acrylate esters of branched and straight chain alkyl alcohols,
  (b) from about 5 to about 70 weight percent of units derived from at least one monomer chosen from (meth)acrylate esters of saturated and unsaturated cyclic alcohols containing 6 to 20 carbon atoms,
  (c) from 0 to about 20 weight percent of units derived from at least one monomer chosen from hydrophilic monomers, and
  (d) from 0 to about 20 weight percent of units derived from at least one monomer other than said (a), (b), and (c) monomers,
  wherein said at least one (meth)acrylic copolymer comprises units derived from at least four different monomers; and
  wherein said composition provides a reshapable effect and a propellant,
  wherein said reshapable effect provides a hair styling that can be modified without adding new material or heat being applied, and
 (2) a dispenser.

36. A method of cosmetically treating hair, comprising applying to the hair before, during, or after shaping of a hairstyle of said hair a composition comprising at least one (meth)acrylic copolymer comprising:
 (a) from about 10 to about 85 weight percent of units derived from at least one monomer chosen from (meth) acrylate esters of branched and straight chain alkyl alcohols,
 (d) from about 5 to about 70 weight percent of units derived from at least one monomer chosen from (meth) acrylate esters of saturated and unsaturated cyclic alcohols containing 6 to 20 carbon atoms,
 (c) from 0 to about 20 weight percent of units derived from at least one monomer chosen from hydrophilic monomers, and
 (d) from 0 to about 20 weight percent of units derived from at least one monomer other than said (a), (b), and (c) monomers,
 wherein said at least one (meth)acrylic copolymer comprises units derived from at least four different monomers; and
 wherein said composition provides a reshapable effect,
 wherein said reshapable effect provides a hair styling that can be modified without adding new material or heat being applied.

37. A method of reshaping hair, comprising:
(1) applying to the hair before, during, or after the initial shaping of the hairstyle a composition comprising at least one (meth)acrylic copolymer comprising:
  (a) from about 10 to about 85 weight percent of units derived from at least one monomer chosen from (meth)acrylate esters of branched and straight chain alkyl alcohols,
  (b) from about 5 to about 70 weight percent of units derived from at least one monomer chosen from (meth)acrylate esters of saturated and unsaturated cyclic alcohols containing 6 to 20 carbon atoms,
  (c) from 0 to about 20 weight percent of units derived from at least one monomer chosen from hydrophilic monomers, and
  (d) from 0 to about 20 weight percent of units derived from at least one monomer other than said (a), (b), and (c) monomers,
  wherein said at least one (meth)acrylic copolymer comprises units derived from at least four different monomers; and
  wherein said composition provides a reshapable effect,
  wherein said reshapable effect provides a hair styling that can be modified without adding new material or heat being applied, and
(2) thereafter shaping the hairstyle at least once, wherein no additional composition or heat is added.

38. A method of manufacturing a reshapable hair styling composition comprising including in a hair styling composition at least one (meth)acrylic copolymer comprising:
  (a) from about 10 to about 85 weight percent of units derived from at least one monomer chosen from (meth)acrylate esters of branched and straight chain alkyl alcohols,
  (b) from about 5 to about 70 weight percent of units derived from at least one monomer chosen from (meth)acrylate esters of saturated and unsaturated cyclic alcohols containing 6 to 20 carbon atoms,
  (c) from 0 to about 20 weight percent of units derived from at least one monomer chosen from hydrophilic monomers, and
  (d) from 0 to about 20 weight percent of units derived from at least one monomer other than said (a), (b), and (c) monomers,
  wherein said at least one (meth)acrylic copolymer comprises units derived from at least four different monomers; and
  wherein said at least one (meth)acrylic copolymer is present in an amount effective to provide a reshapable effect,
  wherein said reshapable effect provides a hair styling that can be modified without adding new material or heat being applied.

39. A reshapable hair styling composition comprising at least one (meth)acrylic copolymer comprising:
  (a) optional units derived from at least one monomer chosen from (meth)acrylate esters of branched and straight chain alkyl alcohols,
  (b) optional units derived from at least one monomer chosen from (meth)acrylate esters of saturated and unsaturated cyclic alcohols containing 6 to 20 carbon atoms,
  (c) optional units derived from at least one monomer chosen from hydrophilic monomers, or
  (d) optional units derived from at least one monomer other than said (a), (b), and (c) monomers,
  wherein said at least one (meth)acrylic copolymer comprises units derived from at least four different monomers,
  wherein said at least one (meth)acrylic copolymer comprises at least one unit derived from monomers recited in either (a) or (b), and
  wherein said composition provides a reshapable effect,
  wherein said reshapable effect provides a hair styling that can be modified without adding new material or heat being applied.

40. The composition according to claim 39, wherein the composition further comprises a cosmetically acceptable vehicle.

41. The composition according to claim 39, wherein said at least one monomer recited in (a) is chosen from (meth)acrylate esters of $C_1$ to $C_{30}$ branched and straight chain alkyl alcohols.

42. The composition according to claim 39, wherein said at least one monomer recited in (a) is chosen from (meth)acrylate esters of $C_4$ to $C_{18}$ branched and straight chain alkyl alcohols.

43. The composition according to claim 39, wherein said at least one monomer recited in (a) is chosen from isooctyl (meth)acrylate, n-butyl (meth)acrylate, isobutyl (meth)acrylate, t-butyl (meth)acrylate, 2-methylbutyl (meth)acrylate, 2-ethylhexyl (meth)acrylate, n-octyl (meth)acrylate, isononyl (meth)acrylate, lauryl (meth)acrylate, and octadecyl (meth)acrylate.

44. The composition according to claim 39, wherein said at least one monomer recited in (b) is chosen from bicyclo heptyl (meth)acrylate, adamantyl (meth)acrylate, 3,5-dimethyladamantyl (meth)acrylate, isobornyl (meth)acrylate, tolyl (meth)acrylate, phenyl (meth)acrylate, t-butylphenyl (meth)acrylate, 2-napthyl (meth)acrylate, benzyl (meth)acrylate, cyclohexyl (meth)acrylate, menthyl (meth)acrylate, 3,3,5-trimethylcyclohexyl (meth)acrylate, dicyclopentenyl (meth)acrylate, and 2-(dicyclopentenyloxy) ethyl (meth)acrylate.

45. The composition according to claim 39, wherein said at least one monomer recited in (c) is chosen from (meth)acrylic acid and N-vinyl-2-pyrrolidone.

46. The composition according to claim 39, wherein said at least one monomer recited in (d) is chosen from vinyl esters, vinyl chlorides, vinylidene chlorides, styrenes, (meth)acrylate esters of $C_1$ to $C_3$ alkyl alcohols, monoacrylic functional polystyrene, and polydimethylsiloxane.

47. The composition according to claim 39, wherein said at least one (meth)acrylic copolymer is present in an amount ranging from about 0.1 to about 40 weight percent of the total weight percent of the composition.

48. The composition according to claim 47, wherein the amount of said at least one (meth)acrylic copolymer ranges from about 0.5 to about 15 weight percent.

49. The composition according to claim 39, wherein said at least one (meth)acrylic copolymer has a Tg ranging from about $-100°$ C. to about $15°$ C.

50. The composition according to claim 39, wherein the composition further comprises at least one additional polymer.

51. The composition according to claim 50, wherein said at least one additional polymer is chosen from anionic, cationic, amphoteric, and nonionic polymers.

52. The composition according to claim 39, further comprising at least one conventional cosmetic constituent chosen from preservatives, perfumes, active hair care agents, plasticizers, anionic, cationic, amphoteric, and nonionic surfactants, hair conditioning agents, silicone fluids, fatty esters, fatty alcohol, long chain hydrocarbons, emollients, lubricants, penetrants, lanolin compounds, protein hydrolysates, other protein derivatives, dyes, tins, bleaches, reducing agents, pH adjusting agents, sunscreens, and thickening agents.

53. A reshapable hair styling composition comprising at least one (meth)acrylic copolymer comprising:
    (a) optional units derived from at least one monomer chosen from (meth)acrylate esters of branched and straight chain alkyl alcohols,
    (b) optional units derived from at least one monomer chosen from (meth)acrylate esters of saturated and unsaturated cyclic alcohols containing 6 to 20 carbon atoms,
    (c) optional units derived from at least one monomer chosen from hydrophilic monomers, or
    (d) optional units derived from at least one monomer other than said (a), (b), and (c) monomers,
    wherein said at least one (meth)acrylic copolymer comprises units derived from at least four different monomers,
    wherein said at least one (meth)acrylic copolymer comprises at least one unit derived from monomers recited in either (a) or (b), and
    wherein said composition provides a reshapable effect and is in the form of a spray, aerosol, mousse, gel, stick, mud, or lotion,
    wherein said reshapable effect provides a hair styling that can be modified without adding new material or heat being applied.

54. An aerosol device comprising a vessel, which comprises:
    (1) an aerosol composition, which provides a reshapable effect and comprises a liquid phase comprising at least one composition comprising at least one (meth)acrylic copolymer comprising:
        (a) optional units derived from at least one monomer chosen from (meth)acrylate esters of branched and straight chain alkyl alcohols,
        (b) optional units derived from at least one monomer chosen from (meth)acrylate esters of saturated and unsaturated cyclic alcohols containing 6 to 20 carbon atoms,
        (c) optional units derived from at least one monomer chosen from hydrophilic monomers, or
        (d) optional units derived from at least one monomer other than said (a), (b), and (c) monomers,
        wherein said at least one (meth)acrylic copolymer comprises units derived from at least four different monomers,
        wherein said at least one (meth)acrylic copolymer comprises at least one unit derived from monomers recited in either (a) or (b), and
        wherein said composition provides a reshapable effect and a propellant,
        wherein said reshapable effect provides a hair styling that can be modified without adding new material or heat being applied, and
    (2) a dispenser.

55. A method of cosmetically treating hair, comprising applying to the hair before, during, or after shaping of a hairstyle of said hair a composition comprising at least one (meth)acrylic copolymer comprising:
    (a) optional units derived from at least one monomer chosen from (meth)acrylate esters of branched and straight chain alkyl alcohols,
    (b) optional units derived from at least one monomer chosen from (meth)acrylate esters of saturated and unsaturated cyclic alcohols containing 6 to 20 carbon atoms,
    (c) optional units derived from at least one monomer chosen from hydrophilic monomers, or
    (d) optional units derived from at least one monomer other than said (a), (b), and (c) monomers,
    wherein said at least one (meth)acrylic copolymer comprises units derived from at least four different monomers,
    wherein said at least one (meth)acrylic copolymer comprises at least one unit derived from monomers recited in either (a) or (b), and
    wherein said composition provides a reshapable effect,
    wherein said reshapable effect provides a hair styling that can be modified without adding new material or heat being applied.

56. A method of reshaping hair, comprising:
    (1) applying to the hair before, during, or after the initial shaping of the hairstyle a composition comprising at least one (meth)acrylic copolymer comprising:
        (a) optional units derived from at least one monomer chosen from (meth)acrylate esters of branched and straight chain alkyl alcohols,
        (b) optional units derived from at least one monomer chosen from (meth)acrylate esters of saturated and unsaturated cyclic alcohols containing 6 to 20 carbon atoms,
        (c) optional units derived from at least one monomer chosen from hydrophilic monomers, or
        (d) optional units derived from at least one monomer other than said (a), (b), and (c) monomers,
        wherein said at least one (meth)acrylic copolymer comprises units derived from at least four different monomers,
        wherein said at least one (meth)acrylic copolymer comprises at least one unit derived from monomers recited in either (a) or (b), and
        wherein said composition provides a reshapable effect,
        wherein said reshapable effect provides a hair styling that can be modified without adding new material or heat being applied, and
    (2) thereafter shaping the hairstyle at least once, wherein no additional composition or heat is added.

57. A method of manufacturing a reshapable hair styling composition comprising including in a hair styling composition at least one (meth)acrylic copolymer comprising:
    (a) optional units derived from at least one monomer chosen from (meth)acrylate esters of branched and straight chain alkyl alcohols,
    (b) optional units derived from at least one monomer chosen from (meth)acrylate esters of saturated and unsaturated cyclic alcohols containing 6 to 20 carbon atoms,
    (c) optional units derived from at least one monomer chosen from hydrophilic monomers, or (d) optional units derived from at least one monomer other than said (a), (b), and (c) monomers, wherein said at least one (meth)acrylic copolymer comprises units derived from at least four different monomers, wherein said at least one (meth)acrylic copolymer comprises at least one unit derived from monomers recited in either (a) or (b), and wherein said at least one (meth)acrylic copolymer is present in an amount effective to provide a reshapable effect, wherein said reshapable effect provides a hair styling that can be modified without adding new material or heat being applied.

* * * * *

UNITED STATES PATENT AND TRADEMARK OFFICE
CERTIFICATE OF CORRECTION

PATENT NO.        : 7,122,175 B2
APPLICATION NO.   : 10/395064
DATED             : October 17, 2006
INVENTOR(S)       : Isabelle Rollat, Henri Samain and Olivier Morel It is certified that error appears in the above-identified patent and that said Letters Patent is hereby corrected as shown below:

In claim 11, column 26, line 32, "150° C." should read --15° C.--.

In claim 14, column 26, line 46, "tins," should read --tints,--.

In claim 15, column 26, line 67, "lotions," should read --lotion,--.

In claim 15, column 27, line 2, "be restored or modified" should read --be modified--.

In claim 24, column 29, line 2, "lauryl(meth)acrylate," should read --lauryl(meth)acrylate,--.

In claim 33, column 29, line 45, "tins" should be --tints,--.

In claim 44, column 32, lines 33-34, "bicyclo heptyl" should read --bicyclo [2.2.1] heptyl--.

In claim 52, column 33, line 8, "tins," should read --tints,--.

Signed and Sealed this

Sixteenth Day of January, 2007

JON W. DUDAS
*Director of the United States Patent and Trademark Office*